United States Patent
Yang et al.

(10) Patent No.: US 12,318,136 B2
(45) Date of Patent: *Jun. 3, 2025

(54) WIRELESS NEUROMODULATION VIA MICROWAVE SPLIT RING RESONATOR

(71) Applicant: Trustees of Boston University, Boston, MA (US)

(72) Inventors: Chen Yang, Newton, MA (US); Ji-Xin Cheng, Newton, MA (US); Nan Zheng, Allston, MA (US); Yueming Li, Brighton, MA (US); Ying Jiang, Brighton, MA (US); Lu Lan, Allston, MA (US); Carolyn Marar, Brighton, MA (US)

(73) Assignee: Trustees of Boston University, Boston, MA (US)

( * ) Notice: Subject to any disclaimer, the term of this patent is extended or adjusted under 35 U.S.C. 154(b) by 120 days.

This patent is subject to a terminal disclaimer.

(21) Appl. No.: 18/089,122

(22) Filed: Dec. 27, 2022

(65) Prior Publication Data

US 2023/0140692 A1 May 4, 2023

Related U.S. Application Data

(63) Continuation of application No. 17/737,710, filed on May 5, 2022, now Pat. No. 11,564,742.

(Continued)

(51) Int. Cl.
*A61B 18/18* (2006.01)
*H01P 7/08* (2006.01)

(52) U.S. Cl.
CPC .......... *A61B 18/1815* (2013.01); *H01P 7/082* (2013.01); *A61B 2018/183* (2013.01); *A61B 2018/1869* (2013.01)

(58) Field of Classification Search
CPC .......... A61B 18/1815; A61B 2018/183; A61B 2018/1869; A61N 5/022; A61N 5/045; H01P 7/082

See application file for complete search history.

(56) References Cited

U.S. PATENT DOCUMENTS 10,492,683 B2 * 12/2019 Yalçinkaya .......... A61B 5/6821
2015/0045866 A1    2/2015 Chen
(Continued)

FOREIGN PATENT DOCUMENTS

WO    2017/136767 A1    8/2017
WO    2020/092652 A1    5/2020

OTHER PUBLICATIONS

A. Marblestone, B. Zamft, Y. Maguire, M. Shapiro, T. Cybulski, J. Glaser, D. Amodei, P. Stranges, R. Kalhor, D. Dalrymple, D. Seo, E. Alon, M. Maharbiz, J. Carmena, J. Rabaey, E. Boyden, G. Church and K. Kording, "Physical Principles for Scalable Neural Recording," Frontiers in computational neuroscience, vol. 7, p. 137, 2013.

(Continued)

*Primary Examiner* — Michael F Peffley
(74) *Attorney, Agent, or Firm* — Cesari and McKenna, LLP; Steven M. Mills

(57) ABSTRACT

A system for neuromodulation includes a split-ring resonator (SRR) comprising a resonance circuit, the SRR being implantable in a cranial target site and a source of microwave signals, wherein the microwave signals are deliverable wirelessly to couple with the SRR to produce a localized electrical field, wherein the localized electrical field inhibits one or more neurons at the cranial target site with submillimeter spatial precision.

49 Claims, 23 Drawing Sheets

Related U.S. Application Data

(60) Provisional application No. 63/185,385, filed on May 7, 2021.

(56) References Cited

U.S. PATENT DOCUMENTS

2020/0061368 A1 2/2020 Towe
2021/0069510 A1* 3/2021 Swoyer .............. A61N 1/36178

OTHER PUBLICATIONS

A. Singer, S. Dutta, E. Lewis, Z. Chen, J.C. Chen, N. Verma, B. Avants, A. K. Feldman, J. O'Malley and M. Beierlein, Magnetoelectric materials for miniature, wireless neural stimulation at therapeutic frequencies, Neuron, vol. 107, No. 4, pp. 631-643 e5, 2020.
A. Yan, L. Lin, C. Liu, J. Shi, S. Na and L. V. Wang, "Microwave-induced thermoacoustic tomography through an adult human skull," Med. Phys., vol. 46, No. 4, p. 1793-1797, 2019.
A.J. Shoffstall, J.E. Paiz, D. M. Miller, G. M. Rial, M. T. Willis, D. M. Menendez, S. R Hostler and J. R. Capadona, Potential for thermal damage to the blood-brain barrier during craniotomy: implications for intracortical recording microelectrodes, Journal of Neural Engineering, vol. 15, p. 034001, 2018.
A.R. Brunoni, M.A. Nitsche, N. Bolognini, M. Bikson, T. Wagner, L. Merabet, D. J. Edwards, A. Valero-Cabre, A. Rotenberg and A. Pascual-Leone, "Clinical research with transcranial direct current stimulation (tDCS): challenges and future directions," Brain Stimulation, vol. 5, No. 3, pp. 175-195, 2012.
A.T. Sidambe, "Biocompatibility of Advanced Manufactured Titanium Implants-Review," Materials (Basel), vol. 7, No. 12, p. 8168-8188,2014.
B. Rosin, M. Slovik, R. Mitelman, M. Rivlin-Etzion, S. N. Haber, Z. Israel, E. Vaadia and H. Bergman, "Closed-loop deep brain stimulation is superior in ameliorating parkinsonism," Neuron , vol. 72, No. 2, pp. 370-384, 2011.
D. K. Piech, B. C. Johnson, K. Shen, M. M. Ghanbari, K. Y. Li, R. M. Neely, J.E. Kay, J.M. Carmena, M. M. Maharbiz and R. Muller, "A wireless millimetre-scale implantable neural stimulator with ultrasonically powered bidirectional communication," Nature Biomedical Engineering, vol. 4, No. 2, pp. 207-222, 2020.
E.A. Navarro, J. Segura, M. Portales and C. Gomez-Perretta de Mateo, "The microwave syndrome: a preliminary study in Spain," Electromagnetic biology and medicine, vol. 22, No. 2-3, pp. 161-169, 2003.
E.S. Boyden, F. Zhang, E. Bamberg, G. Nagel and K. Deisseroth, "Millisecond-timescale, genetically targeted optical control of neural activity," Nature Neuroscience, vol. 8, No. 9, pp. 1263-1268, 2005.
H. S. Mayberg, A. M. Lozano, V. Voon, H. E. McNeely, D. Seminowicz, C. Hamani, J. M. Schwalb and S. H. Kennedy, Deep brain stimulation for treatment-resistant depression, Neuron, vol. 45, No. 5, pp. 651-660., 2005.
H. Wachtel, R. Seaman and W. Joines, "Effects of low intensity microwaves on isolated neurons," Annals of the New York Academy of Sciences, vol. 247, No. 1, pp. 46-62, 1975.
H.B. Chen, J. H. Deng, Q. Cui, B. Chanda and K. Henzler-Wildman, "Mapping temperature-dependent conformational change in the voltage-sensing domain of an engineered heat-activated K+ channel," Proc. Natl. Acad. Sci. USA, vol. 118, p. e2017280118, 2021.
I.A. Titushkin, V. S. Rao, W. F. Pickard, E.G. Moros, G. Shafirstein and M. R Cho, "Altered Calcium Dynamics Mediates P19-Derived Neuron-Like Cell Responses to Millimeter-Wave Radiation," Radiation Research, vol. 172, No. 6, p. 725-736, 2009.
"IEEE Standard for Safety Levels with Respect to Human Exposure to Radio Frequency Electromagnetic Fields, 3 kHz to 300 Ghz," IEEE SID C95.1-2005, 2006, 40 pages.
International Search Report and Written Opinion in corresponding Application No. PCT/US22/27929 dated Aug. 29, 2022 (14 pgs.).
J. Li, S. Liu, W. Liu, Y. Yu and Y. Wu, "Suppression of firing activities in neuron and neurons of network induced by electromagnetic radiation," Nonlinear Dynamics, vol. 83, No. 1-2, pp. 801-810, 2016.
J. Wells, C. Kao, K. Mariappan, J. Albea, E. D. Jansen, P. Konrad and A. Mahadevan-Jansen, "Optical stimulation of neural tissue in vivo," Optics letters, vol. 30, No. 5, pp. 504-506, 2005.
J.C. Lin, "A new IEEE standard for safety levels with respect to human exposure to radio-frequency radiation," IEEE Antennas and Propagation Magazine, vol. 48, No. 1, pp. 157-159, 2006.
J.S. Ho, Y. Tanabe, S. M. Iyer, A. J. Christensen, L. Grosenick, K. Deisseroth, S. L. Delp and A. S. Poon, "Self-tracking energy transfer for neural stimulation in untethered mice," Physical Review Applied, vol. 4, No. 2, p. 024001, 2015.
K. A. Hossmann and D. Hermann,"Effects of electromagnetic radiation of mobile phones on the central nervous system," Bioelectromagnetics: Journal of the Bioelectromagnetics Society, The Society for Physical Regulation in Biology and Medicine, The European Bioelectromagnetics Association, vol. 24, pp. 49-62, 2003.
K. L. Montgomery, A. J. Yeh, J. S. Ho, V. Tsao, S. M. Iyer, L. Grosenick, E. A. Ferenczi, Y. Tanabe, K. Deisseroth and S. L. Delp, Wirelessly powered, fully internal optogenetics for brain, spinal and peripheral circuits in mice, Nature Methods, vol. 12, No. 10, pp. 969-974, 2015.
K. L. Montgomery, A. J. Yeh, J. S. Ho, V. Tsao, S. M. Iyer, L. Grosenick, E. A. Ferenczi, Y. Tanabe, K. Deisseroth, S.L. Delp and A. S. Y. Poon, "Wirelessly powered, fully internal optogenetics for brain, spinal and peripheral circuits in mice," Nature Methods, vol. 12, p. 969-974, 2015.
K.-f. Shen and P.A. Schwartzkroin, "Effects of temperature alterations on population and cellular activities in hippocampal slices from mature and immature rabbit," Brain Research, vol. 475, No. 2, pp. 305-316, 1988.
L.G. Wang, "Measurements and Implications of the Membrane Dipole Potential," Annu. Rev. Biochem., vol. 81, pp. 615-635, 2012.
M. Dogangun, P. E. Ohno, D. Y. Liang, A. C. McGeachy, A.G. Be, N. Dalchand, T. Z. Li, Q. Cui and F. M. Geiger, Hydrogen-Bond Networks near Supported Lipid Bilayers from Vibrational Sum Frequency Generation Experiments and Atomistic Simulations, J. Phys. Chem. B., vol. 122, pp. 4870-4879, 2018.
M. E. P. Didier, O. B. Tarun, P. Jourdain, P. Magistretti and S. Roke, "Membrane water for probing neuronal membrane potentials and ionic fluxes at the single cell level," Nature Communications, vol. 9, p. 5287, 2018.
M. G. Shapiro, M. F. Priest, P.H. Siegel and F. Bezanilla, "Thermal Mechanisms of Millimeter Wave Stimulation of Excitable Cells," Biophys J, vol. 104, No. 12, p. 2622-2628, 2013.
M. N. Shneider and M. Pekker, "Non-thermal mechanism of weak microwave fields influence on neurons," Journal of Applied Physics, vol. 114, p. 104701, 2013.
M.A. Fishman, A. Antony, M. Esposito, T. Deer and R. Levy, "The Evolution of Neuromodulation in the Treatment of Chronic Pain: Forward-Looking Perspectives," Pain Medicine, vol. 20, No. S1, p. S58-S68, 2019.
M.A. Maxime Levesquea, "The kainic acid model of temporal lobe epilepsy," Neuroscience & Biobehavioral Reviews, vol. 37, No. 10, pp. 2887-2899, 2013.
N. binti Ismail and M. Z. bin Mohd Jenu, "In Modeling of electromagnetic wave penetration in a human head due to emissions from cellular phone," 2007 Asia-Pacific Conference on Applied Electromagnetics, IEEE, pp. 1-5, 2007.
N. Ikeda, O. Hayashida, H. Kameda, H. Ito and T. Matsuda, "Experimental study on thermal damage to dog normal brain," International Journal of Hyperthermia, vol. 10, No. 4, pp. 553-561, 1994.
N. McDannold, N. Vykhodtseva, F. A. Jolesz and K. Hynynen, "MRI investigation of the threshold for thermally induced blood-brain barrier disruption and brain tissue damage in the rabbit brain," Magnetic Resonance in Medicine, vol. 51, No. 5, pp. 913-923, 2004.
P. Boon, K. Vonck, V. De Herdt, A. Van Dycke, M. Goethals, L. Goossens, M. Van Zandijcke, T. De Smedt, I. Dewaele and R. Achten, "Deep brain stimulation in patients with refractory temporal lobe epilepsy," Epilepsia, vol. 48, No. 8, pp. 1551-1560, 2007.

(56) References Cited

OTHER PUBLICATIONS

P. Davis and J. Gaitanis, "Neuromodulation for the Treatment of Epilepsy: A Review of Current Approaches and Future Directions," Clinical Therapeutics, vol. 42, No. 7, pp. 1140-1154, 2020.
P.S. Yarmolenko, E. J. Moon, C. Landon, A. Manzoor, D. W. Hochman, B. L. Viglianti and M. W. Dewhirst, Thresholds for thermal damage to normal tissues: An update, International Journal of Hyperthermia, vol. 27, No. 4, pp. 320-343, 2011.
R. C. Beason and P. Semm, "Responses of neurons to an amplitude modulated microwave stimulus," Neuroscience Letters, vol. 333, No. 3, pp. 175-178, 2002.
R. Hall, "Pure Rotational Spectrum of Water Vapor," Journal of Chemical Physics, vol. 47, No. 7, p. 2454, 1967.
S. Chowdhury, B. W. Jarecki and B. Chanda, "A Molecular Framework for Temperature-Dependent Gating of Ion Channels," Cell, vol. 158, pp. 1148-1158., 2014.
S. Romanenko, P.H. Siegel, D. A. Wagenaar and V. Pikov, "Effects of millimeter wave irradiation and equivalent thermal heating on the activity of individual neurons in the leech ganglion," Journal of Neurophysiology, vol. 112, No. 10, pp. 2423-2431, 2014.
T. Mohoric and U. Bren, "How does microwave irradiation affect aqueous solutions of polar solutes?," J. Mol. Liqud., vol. 266, pp. 218-228, 2018.
T. Mohoric and U. Bren, "Microwave irradiation affects ion pairing in aqueous solutions of alkali halide salts," J. Chem. Phys., vol. 146, p. 044504, 2017.
V. Walsh and A. Cowey, "Transcranial magnetic stimulation and cognitive neuroscience," Nature Reviews Neuroscience, vol. 1, No. 1, pp. 73-80., 2000.
Y. Jiang, H.J. Lee, L. Lan, H.-a. Tseng, C. Yang, H.-Y. Man, X. Han and J.-X. Cheng, "Optoacoustic brain stimulation at submillimeter spatial precision," Nature Communications, vol. 11, No. 1, pp. 1-9, 2020.
Z.-D. Deng, S. H. Lisanby and A. V. Peterchev, "Electric field depth-focality tradeoff in transcranial magnetic 7 stimulation: simulation comparison of 50 coil designs," Brain stimulation, vol. 6, No. 1, pp. 1-13, 2013.

* cited by examiner

| Device name | Power type | Implant Size (mm³) | Free moving | Modulation type | Penetration depth |
|---|---|---|---|---|---|
| Micro LED [45, 25] | Radio frequency | 25-50 | Y | excitation | Several cm |
| Stim Dust [27] | piezoelectric | 10 | N | excitation | Several cm |
| Magneto-electric stimulator [28] | magnetic field | 175-500 | Y | excitation | Several cm |
| Microwave SRR (this work) | Microwave (1.0-2.5 GHz) | 1.8 | Y | inhibition | Several cm |

WIRELESS NEUROMODULATION VIA MICROWAVE SPLIT RING RESONATOR

CROSS-REFERENCE TO RELATED APPLICATIONS

This application is a continuation of U.S. patent application Ser. No. 17/737,710, filed on May 5, 2022, now issued U.S. Pat. No. 11,564,742, which is related to and claims the benefit of U.S. Provisional Application No. 63/185,385, filed on May 7, 2021, each of which is incorporated herein by reference in its entirety.

STATEMENT OF GOVERNMENT SUPPORT

This invention was made with Government Support under Grant No. NS109794 awarded by the National Institutes of Health. The Government has certain rights in the invention.

BACKGROUND

1. Technical Field

The present disclosure is related to an implantable split-ring resonator (SRR) and, in particular, to a system and method for an implantable split-ring resonator (SRR) that generates a localized and enhanced microwave field at the gap site with submillimeter spatial precision.

2. Discussion of Related Art

Neuromodulation is a rapidly expanding field that has applications in neuroscience research, disease diagnosis, and treatment. Neuromodulation devices are seeing greater use in the clinic for the treatment of conditions such as depression, epilepsy, and chronic pain. Of these techniques, deep brain stimulation (DBS) is the most widely used, delivering electrical current via an implanted electrode to deep brain regions. The electrode, however, must be physically connected to a subcutaneously implanted stimulator. This requirement makes the device highly invasive, as surgery is required to change the stimulator battery.

Electromagnetic waves, such as radio-frequency waves, have been used to noninvasively modulate various biological systems. For example, transcranial direct current stimulation (tDCS) and transcranial magnetic stimulation (TMS) have successfully reached the deep brain to treat Parkinson's Disease, depression, and epilepsy. However, due to the long wavelength (tens of meters) of the electromagnetic waves employed, tDCS and TMS offer poor spatial resolution of a few centimeters. Photons have sub-micron wavelength and provide single-cell modulation through optogenetics. Yet, the strong tissue scattering prevents photons from noninvasively reaching deep tissue. More recently, optical fiber-based optoacoustic neural stimulation has demonstrated sub-millimeter spatial resolution, but the need for optical fiber implantation prevents wireless implementation.

SUMMARY

According to one aspect, a system for neuromodulation is provided. The system includes a split-ring resonator (SRR) which includes a resonance circuit. The SRR is implantable in a cranial target site. The system also includes a source of microwave signals. The microwave signals are deliverable wirelessly to couple with the SRR to produce a localized electrical field, and the localized electrical field inhibits one or more neurons at the cranial target site with submillimeter spatial precision.

In some exemplary embodiments, the SRR is powered wirelessly by the microwave signals. In other exemplary embodiments, the SRR has a perimeter of approximately one half of the microwave wavelength and functions as a resonant antenna.

In some exemplary embodiments, the SRR has a volume of no more than 1.8 mm$^3$. In other exemplary embodiments, the SRR allows wireless neural inhibition at centimeter-scale depths. Additionally, the wireless neural inhibition at centimeter-scale depths can enable deep-tissue modulation for the treatment of disorders involving excessive excitability.

In some exemplary embodiments, the submillimeter wavelength spatial precision enables region-specific brain modulation or selective inhibition of a single nerve. In other exemplary embodiments, the submillimeter wavelength spatial precision is in the order of 100 μm. In other exemplary embodiments, the SRR enables lower microwave dosage to meet safety limits of 10 W/kg averaged over 6 minutes, which corresponds to an average dosage of 3600 J/kg. Additionally, the lower microwave dosage can prevent thermal damage.

In some exemplary embodiments, the SRR can be adjusted to tune a resonance frequency of the SRR. In other exemplary embodiments, the localized electrical field inhibiting one or more neurons at the cranial target site comprises neural activity with a reduced firing rate for up to 50 seconds after the microwave signals are delivered to the cranial target site. Additionally, the reduced firing rate for up to 50 seconds after the microwave signals are delivered to the cranial target site is not induced by damage to the one or more neurons.

In some exemplary embodiments, the SRR comprises copper. In other exemplary embodiments, the SRR comprises titanium alloy. In other exemplary embodiments, the microwave signals are pulsed signals. Additionally, the microwave signals can undergo pulse modification to prolong microwave treatment without inducing thermal toxicity.

In some exemplary embodiments, one or more SRRs with varying diameter may be implanted at a cranial target site to modulate multiple brain regions. In other exemplary embodiments, the microwave signals are delivered at dosages below the safe exposure limit.

According to another aspect, a method for neuromodulation is provided. The method includes implanting a split-ring resonator (SRR) comprising a resonance circuit, the SRR being implantable in a cranial target site. The method also includes delivering a source of microwave signals, wherein the source of microwave signals are deliverable wirelessly to couple with the SRR to produce a localized electrical field, wherein the localized electrical field inhibits one or more neurons at the cranial target site with submillimeter spatial precision.

According to another aspect, a method for manufacturing a split-ring resonator (SRR) is provided. The method includes coating a surface of a substrate with a lift-off resist (LOR) first layer. The method also includes coating the LOR first layer with a lithography resist second layer to form a bi-layer. The method further includes patterning the lithography resist layer and depositing a metal on the patterned resist later by electron beam deposition to create a patterned metal layer through lift-off process.

BRIEF DESCRIPTION OF THE DRAWINGS

The present disclosure is further described in the detailed description which follows, in reference to the noted plurality of drawings by way of non-limiting examples of embodiments of the present disclosure, in which like reference numerals represent similar parts throughout the several views of the drawings.

FIG. 1A is a simulated temperature heat map of SRR under microwave irradiation. FIG. 1B is a profile of cross section of FIG. 1A. FIG. 1C includes thermal images of 4.94 mm SRR before, during, and after is 1 s MW irradiation at 2.0 GHz and 2 W/cm² demonstrating hotspot formation at the gap. FIG. 1D includes thermal images of the maximum temperature change at SRR gap and simulated normalized MW intensity for given MW frequencies. FIG. 1E is a graph of simulated electric field intensity at given frequencies for SRRs of varying diameter.

FIG. 2A is a GCaMP fluorescence heatmap for neurons. FIG. 2B shows single cell traces for neurons in FIG. 2A. FIG. 2C is a graph showing thermal changes in medium. FIG. 2D is a schematic of in vitro experiments with SRR. FIG. 2E is an image of showing the SRR was submerged in medium and placed ~100 μm from neurons. FIGS. 2F-2G are graphs showing graph lines of the various sites highlighted in FIG. 2E. FIGS. 2I-2L are GCaMP fluorescence heatmap calcium traces for single neurons at varying distances near the SRR gap. FIG. 2M is a GCaMP fluorescence heatmap for neurons under 0.2 W/cm² MW at 2.0 GHz for 3 s without SRR.

DETAILED DESCRIPTION

According to the system and method of the present disclosure, an implantable split-ring resonator (SRR) that generates a localized and enhanced microwave field at the gap site with submillimeter spatial precision is provided. According to the technology of the disclosure, the SRR can break the microwave diffraction limit and greatly enhances the efficiency of microwave inhibition. Microwaves, with wavelengths on the order of millimeters, have centimeter-scale penetration depth and have been shown to reversibly inhibit neuronal activity. Yet, microwaves alone do not provide sufficient spatial precision to modulate target neurons without affecting surrounding tissues. With the SRR, microwaves at dosages below the safe exposure limit are shown to inhibit neurons within ~200 μm from the gap site.

Microwaves (MW), with frequencies between 300 MHz and 300 GHz, fill the gap between optical waves and magnetic waves, yet have rarely been explored for neuromodulation. MW have much longer wavelengths than photons and have been known to provide >50 mm penetration depth into the human brain noninvasively, while maintaining more than 50% of their energy. MW wavelengths are also much shorter than those of magnetic waves, promising higher spatial resolution to specifically modulate subcortical regions. Reports of using the non-thermal effect of MW to modulate neural activity date back to the 1970s, where low intensity MW was applied to Aplysia pacemaker neurons for extended time periods (>60 s), and a reversible reduction in the firing rate was observed. The mechanism was attributed to MW perturbation of current flow inside axons. Since then, several studies have focused on the effect of chronic exposure to MW from cell phones, Wi-Fi, and other communication apparatus. However, these studies utilized broadcasted MW that lacks spatial precision, and the extended exposure time increases the risk of thermal damage to both targeted and surrounding tissues.

According to embodiments of the present disclosure, minimally invasive MW neuromodulation at an unprecedented spatial resolution by taking advantage of an implantable split-ring resonator (SRR) design is presented. The SRR can have a perimeter of approximately one half of the MW wavelength, thus acting as a resonant antenna. It couples the MW wirelessly and concentrates it at the gap, producing a localized electrical field, with localization of a MW field to ~200 μm in space via resonance with the MW SRR. The device can allow for neuromodulation beyond the MW diffraction limit, while using power densities below the threshold for safe MW exposure. The present disclosure demonstrates the capability of the MW SRR to inhibit neuronal activity transcranially and with submillimeter spatial precision. Additionally, an application of the MW SRR in an in vivo model of epilepsy is presented.

Figure 1A:
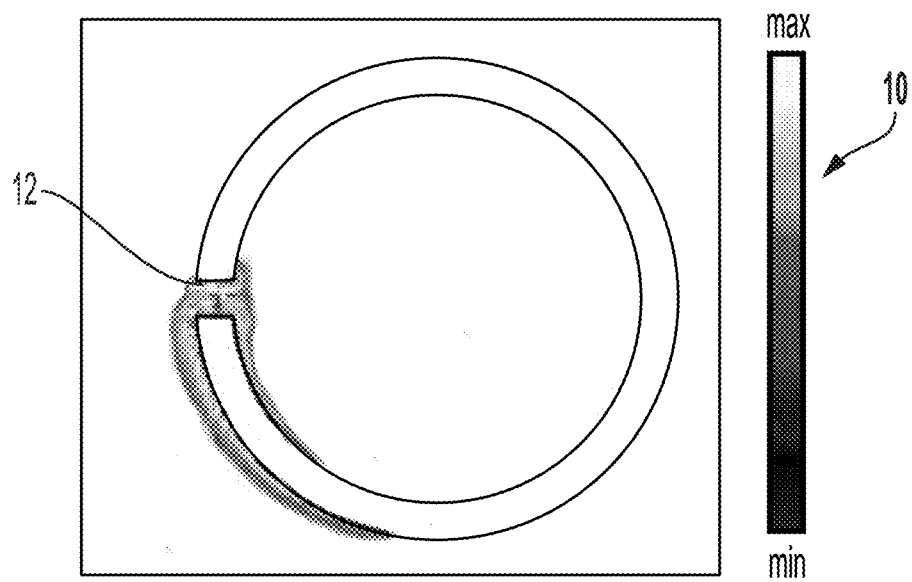
FIGS. 1A-1E show views of the SRR efficiently concentrating microwaves at the gap site.
Figure 1B:
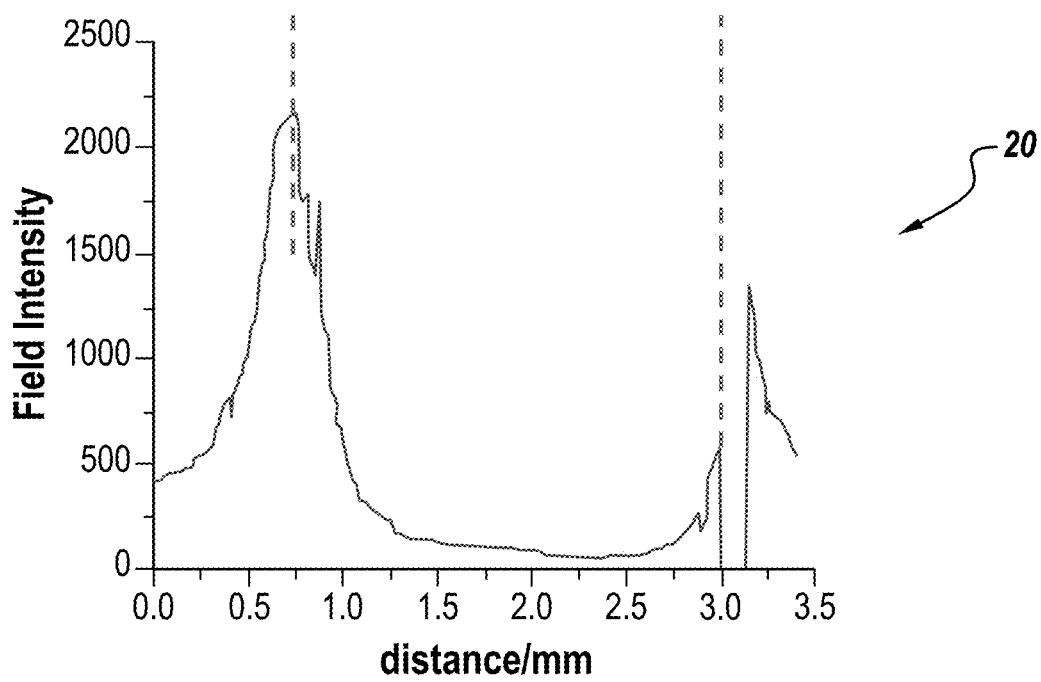

FIGS. 1A-1B show the SRR can efficiently concentrate microwaves at the gap site. The SRR can be modeled as an LC resonance circuit where the ring acts as an inductor L and the gap acts as a capacitor C. When the SRR resonates with the incident MW, a strong electric field is concentrated at the capacitor. To theoretically verify the resonance effect of the SRR and determine the resonance frequency, the present disclosure provides an application of finite element modeling of a copper SRR in bulk phosphate buffered saline (PBS) under an electromagnetic field from 0.1 GHz to 3 GHz in FIGS. 1A and 1B. At 1.5 GHz, a strong electromagnetic field was observed at the gap site 12 with high contrast to the surrounding medium in view of 10 of FIG. 1A. In view 20 in FIG. 1B, the full width half maximum (FWHM) of the MW intensity at the gap 12 was 0.34 mm, whereas the wavelength of the MW was ~200 mm. This indicates a strong resonance effect and high spatial confinement of the MW field. The SRR generates concentrated MW at the ring gap 12 with an enhancement factor of 200 compared to the MW intensity in the surrounding medium. The field intensity at the gap 12 drops significantly at higher or lower frequencies, indicating that no resonance effect was observed at off-resonance frequencies.

Figure 1C:
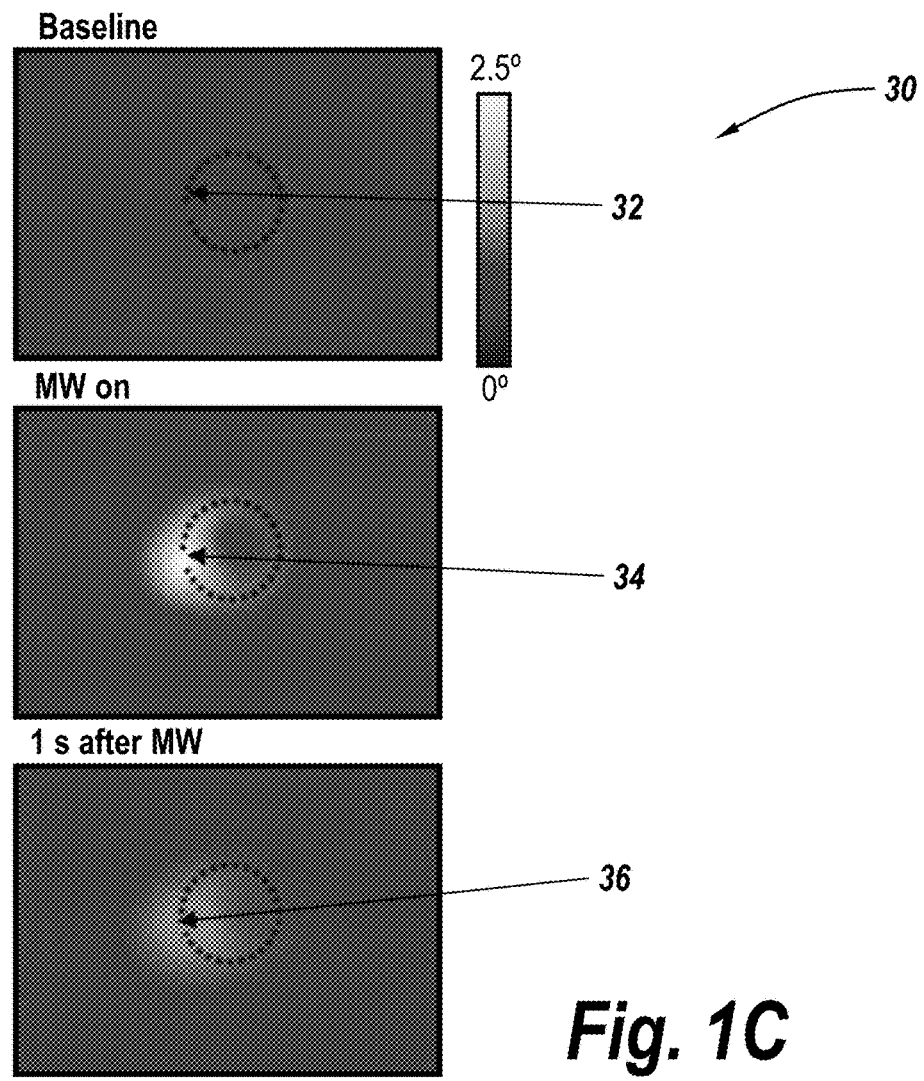
Figure 1D:
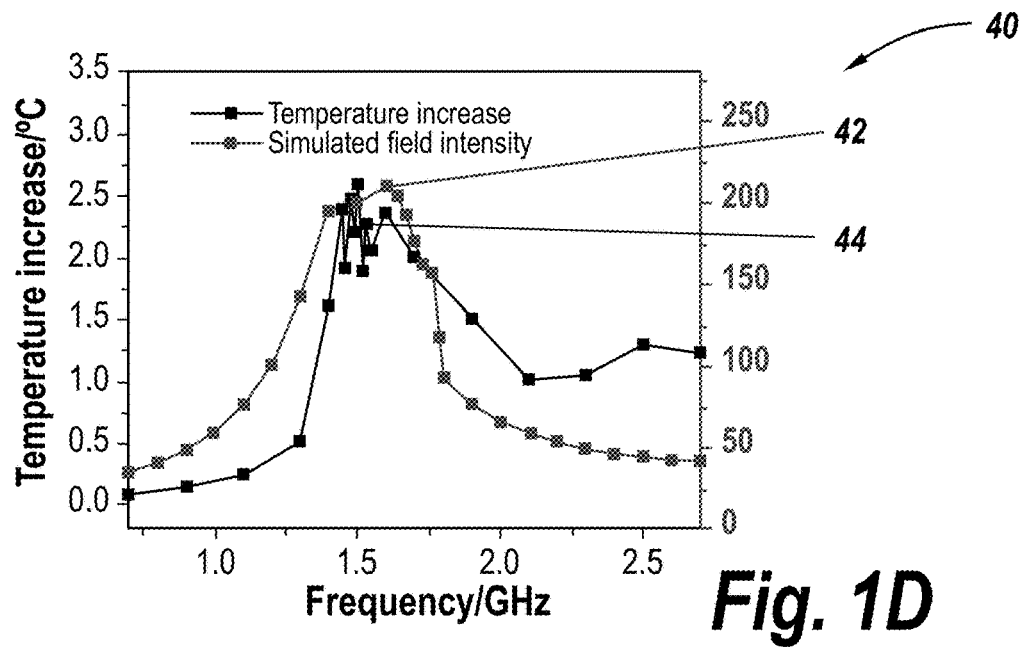
Figure 1E:
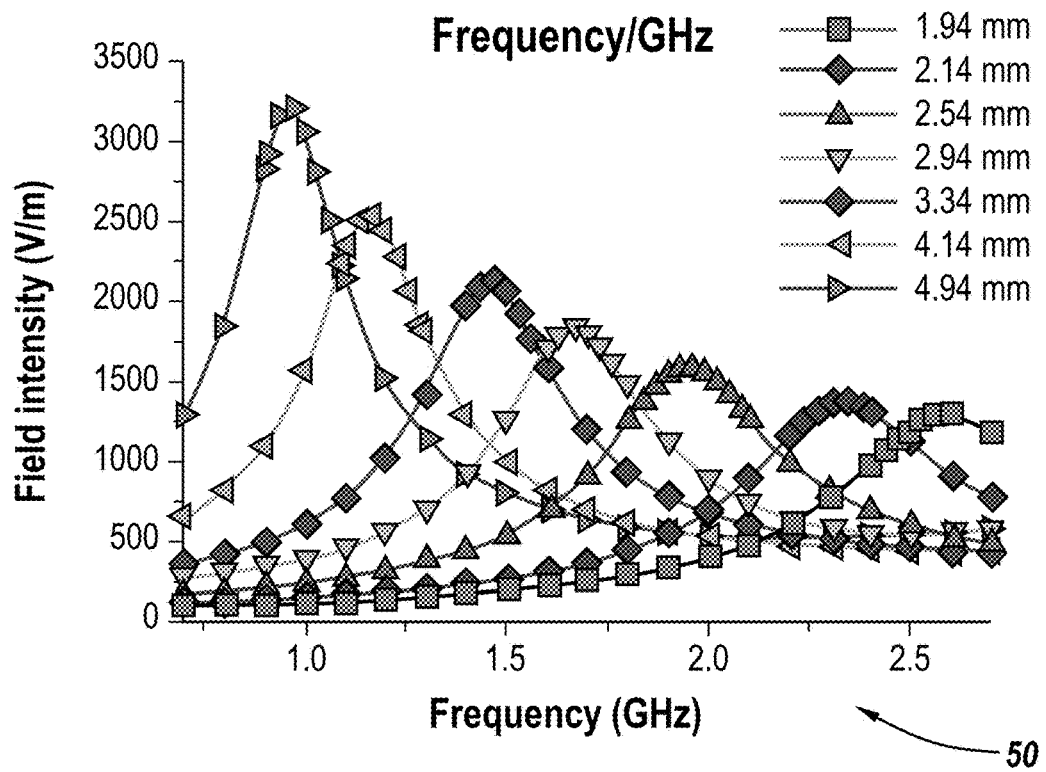

FIGS. 1C-1E experimentally validate these findings with views 30, 40, and 50 respectively of a copper ring (outer diameter 2.56 mm, gap 0.2 mm, height 0.2 mm and width 0.03 mm) fabricated through laser cutting. According to the illustrative embodiment, the ring can be placed at the air-water interface and imaged with a thermal camera. MW can be delivered through a wave guide with the magnetic field perpendicular to the ring plane at 2 W/cm². Thermal images 32, 34, and 36 shown in view 30 of FIG. 1C provide visual evidence of the hot spot at the SRR gap. Such hot spot confirms a localized, enhanced electric field predicted by the simulation of the present implementation. To validate the resonance effect, temperature increase 42 at the gap can be measured under 1 s of MW irradiation at frequencies ranging from 0.7 GHz to 2.7 GHz at graph lines 42 against simulated field intensity graph line 44, as presented in view 40. In FIG. 1D, maximum temperature increase of 2.51° C. can be observed at the gap site at 1.5 GHz, in accordance with the resonance frequency determined by the simulation. At off-resonance frequencies, the maximum temperature increase 42 was less than 0.13° C. The resonance frequency in an LC circuit is defined as $$f = \frac{1}{2\pi\sqrt{LC}}.$$

Thus, increasing the perimeter of the ring increases the inductance and consequently decreases the resonance frequency. FIG. 1E shows at view 50 that in accordance, the simulation provides that by varying the ring perimeter, the resonance frequency of the ring can be tuned. Collectively, this illustrative example provides that the SRR generates a strong electromagnetic field at the gap site with submillimeter spatial precision via the resonance effect.

Figure 3A:
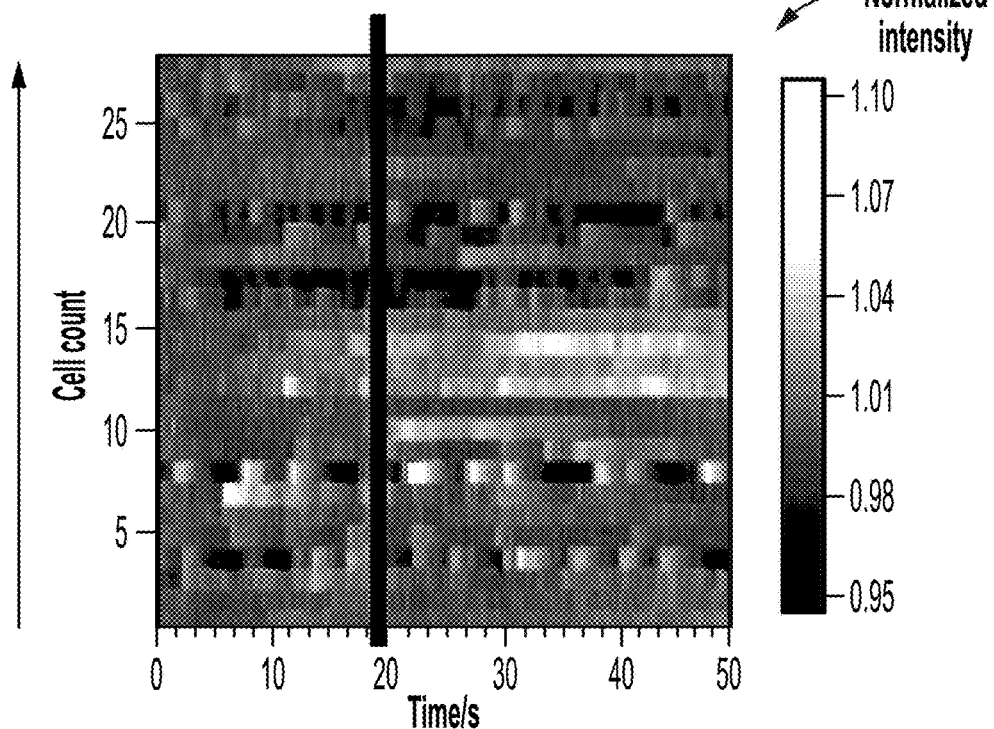
FIG. 3A is a GCaMP fluorescence heatmap of primary neurons spontaneous activity.
Figure 3B:
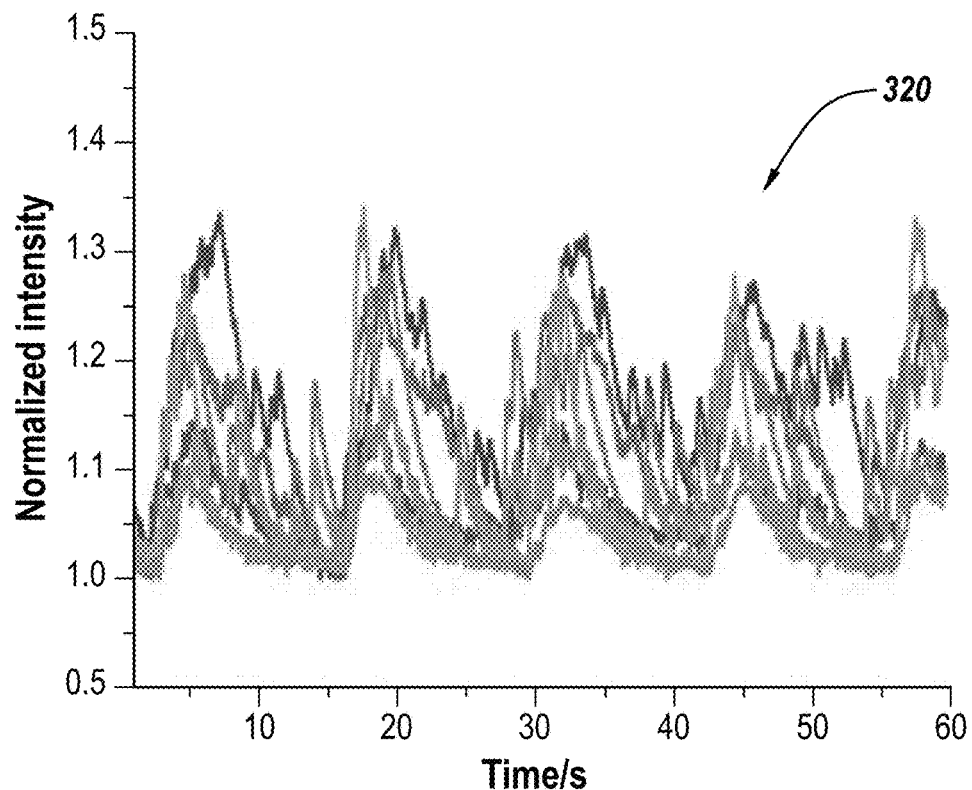
FIG. 3B is a graph of single cell traces for neurons in FIG. 3A.

According to the embodiments of the present disclosure, microwave inhibits neuronal activity via a nonthermal mechanism. MW inhibition of neuronal firing through a non-thermal mechanism has been previously demonstrated in Aplysia pacemaker neurons and avian neurons. To verify that the inhibitory effect also occurs in mammalian neurons, an illustrative embodiment includes exposing cultured primary cortical mouse neurons to a MW field at 1.0 GHz and 2 W/cm² for 3 s. Neuronal activity can be visualized by calcium imaging of GCaMP6f transfected neurons, and as shown in views 310 and 320 of FIGS. 3A and 3B, neurons can exhibit periodic spontaneous activity without microwave treatment. FIG. 3A presents a GCaMP fluorescence heatmap view 310 of primary neurons spontaneous activity, and FIG. 3B shows a graph view 320 of single cell traces for the neurons presented in view 310 of FIG. 3A.

Figure 2A:
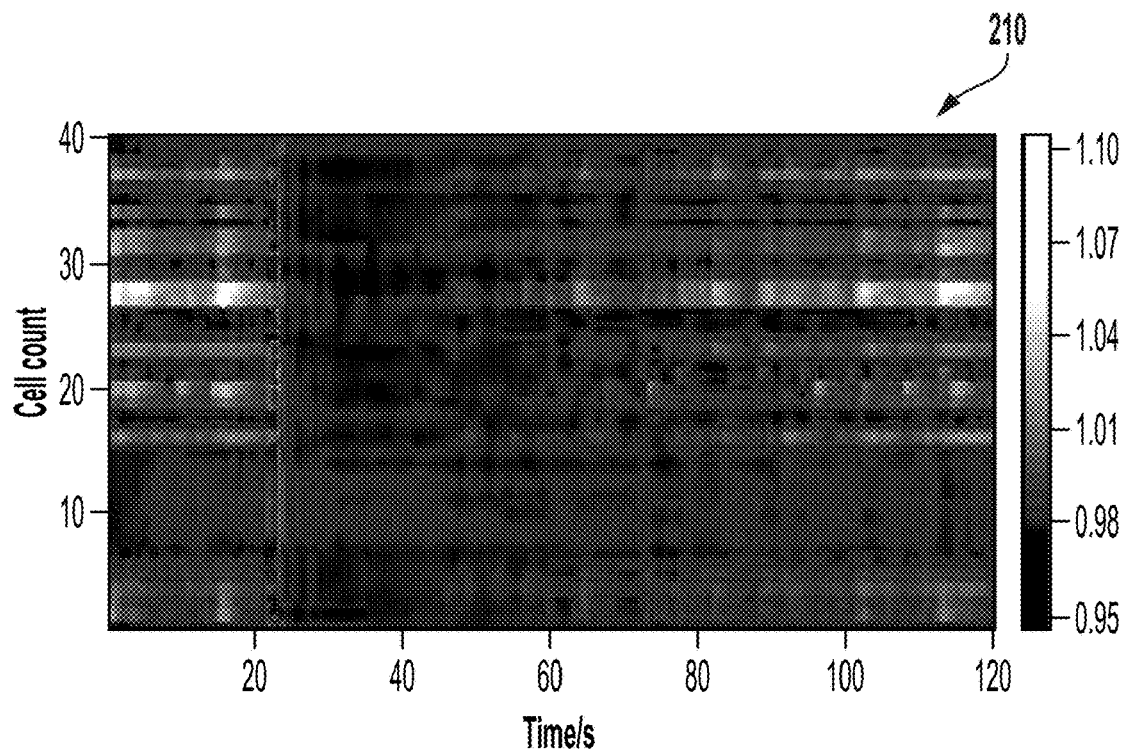
FIGS. 2A-2M show views of microwave SRR inhibiting neuron via a nonthermal mechanism.
Figure 2B:
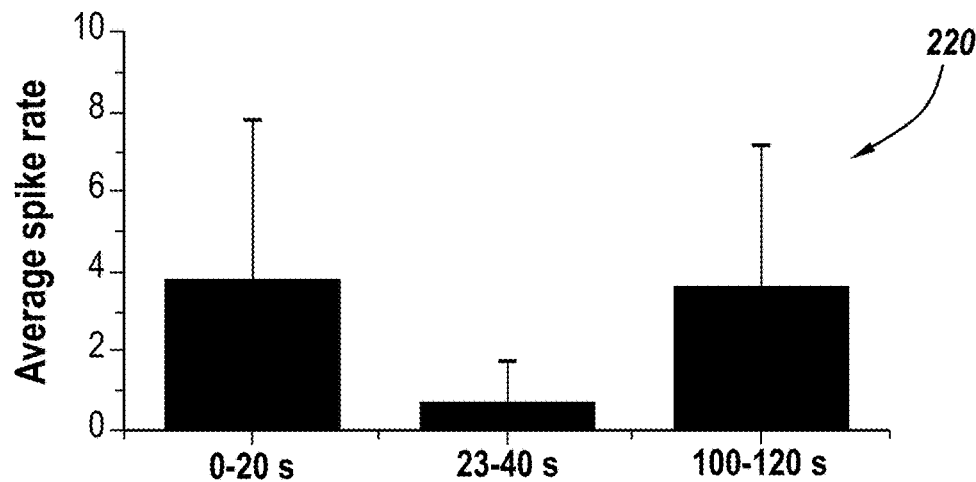
Figure 2C:
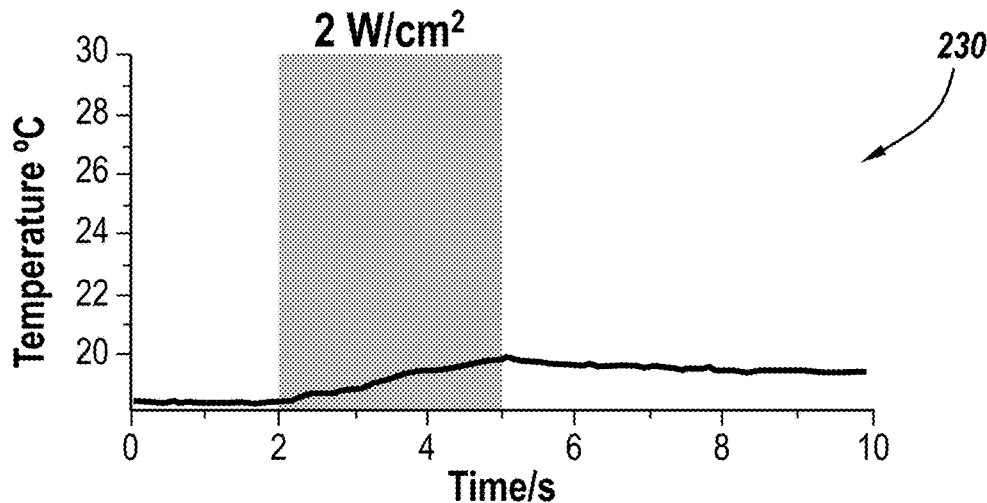

FIGS. 2A-2M show that immediately after MW irradiation, neurons showed reduced firing rate for up to 50 s, after which they resumed their spontaneous firing pattern, as shown in view 210 of FIG. 2A, which provides a GCaMP fluorescence heatmap for neurons under 100 W/cm²MW irradiation at 1.0 GHz for 1 s. According to the illustrative embodiment, this result indicates that the inhibition is not induced by damage of the neurons. In graph view 220 of FIG. 2B, which provides single cell traces for neurons in FIG. 2A, the average inhibition rate was 84% for 3 s of microwave irradiation, compared to only 34% for 0.5 s irradiation. FIG. 2C, which shows thermal change view 230 in medium during 3 s of 100 W/cm² MW irradiation at 1.0 GHz, provides simultaneous thermal imaging of the cell culture under MW irradiation and shows that the temperature increase during 3 s microwave exposure was 1.6° C., which is known to have no significant modulation effect in mammalian neurons. According to the embodiments of the present disclosure, these results confirm the capabilities of MW to inhibit mammalian neurons via a non-thermal mechanism.

Figure 2D:
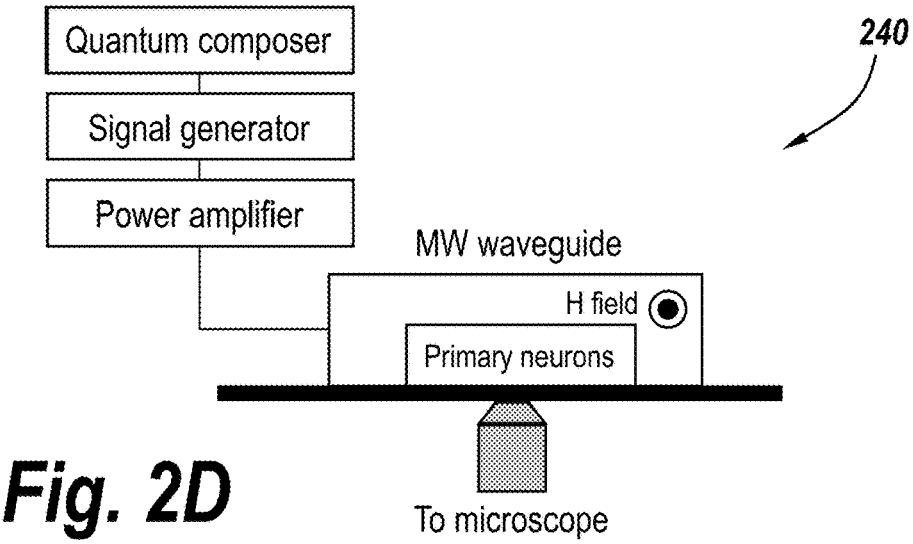
Figure 2E:
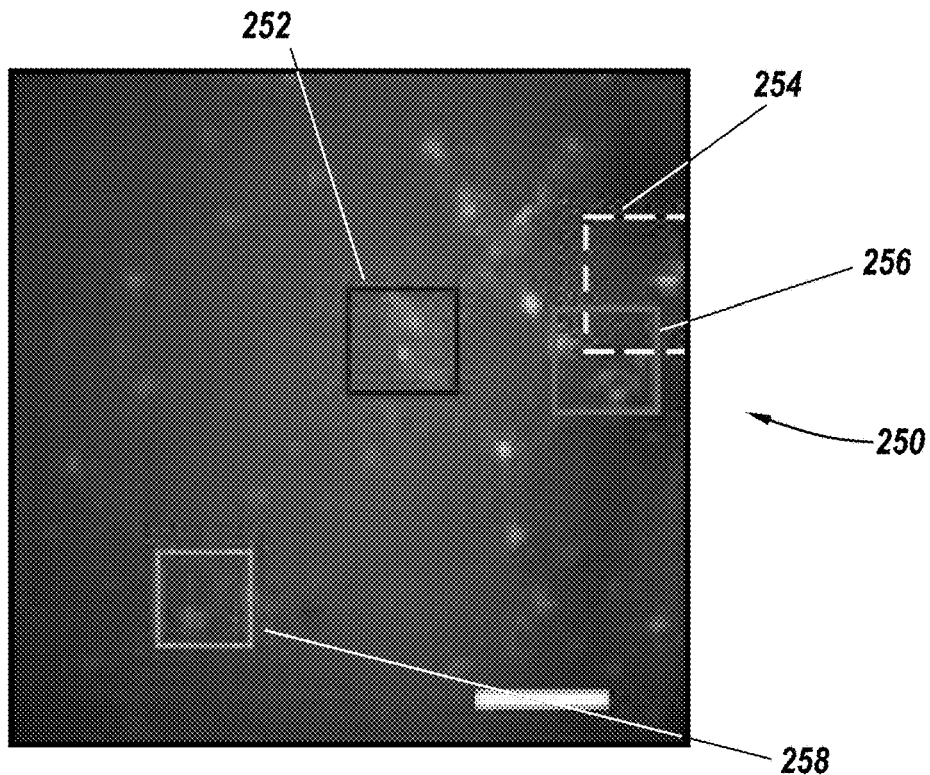
Figure 2F:
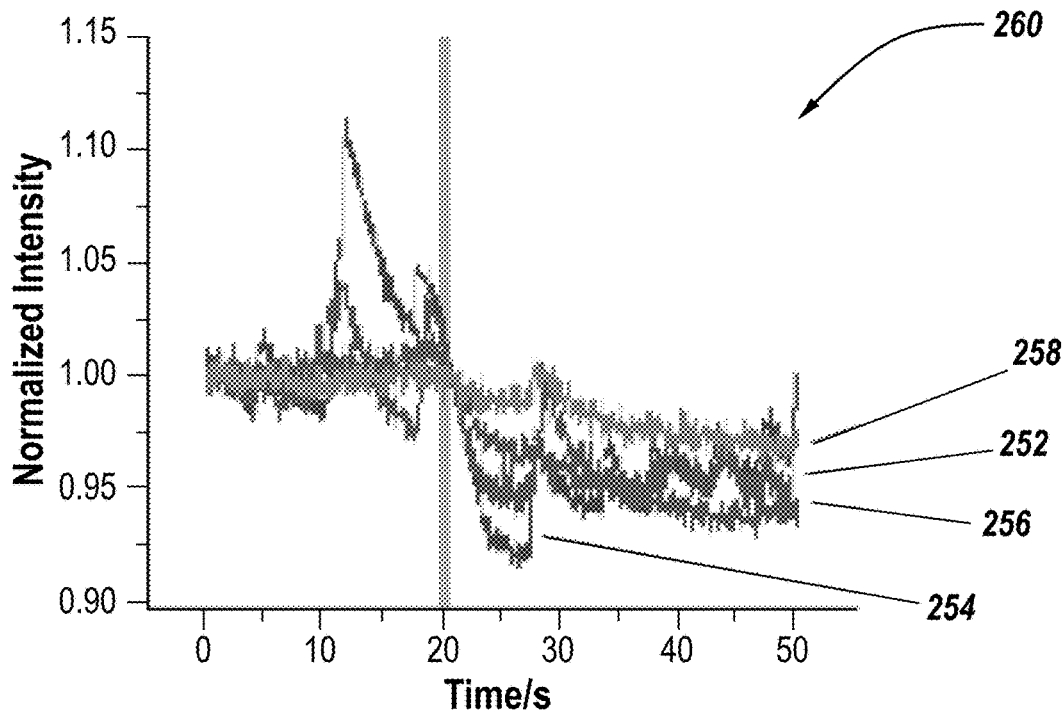
Figure 2G:
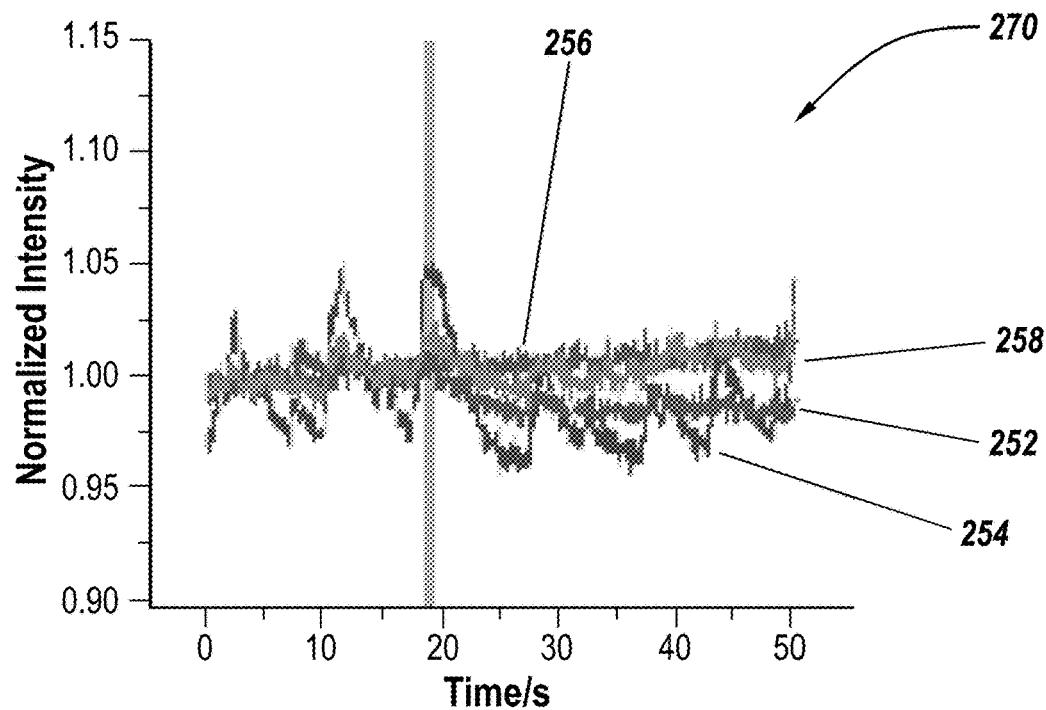
Figure 2H:
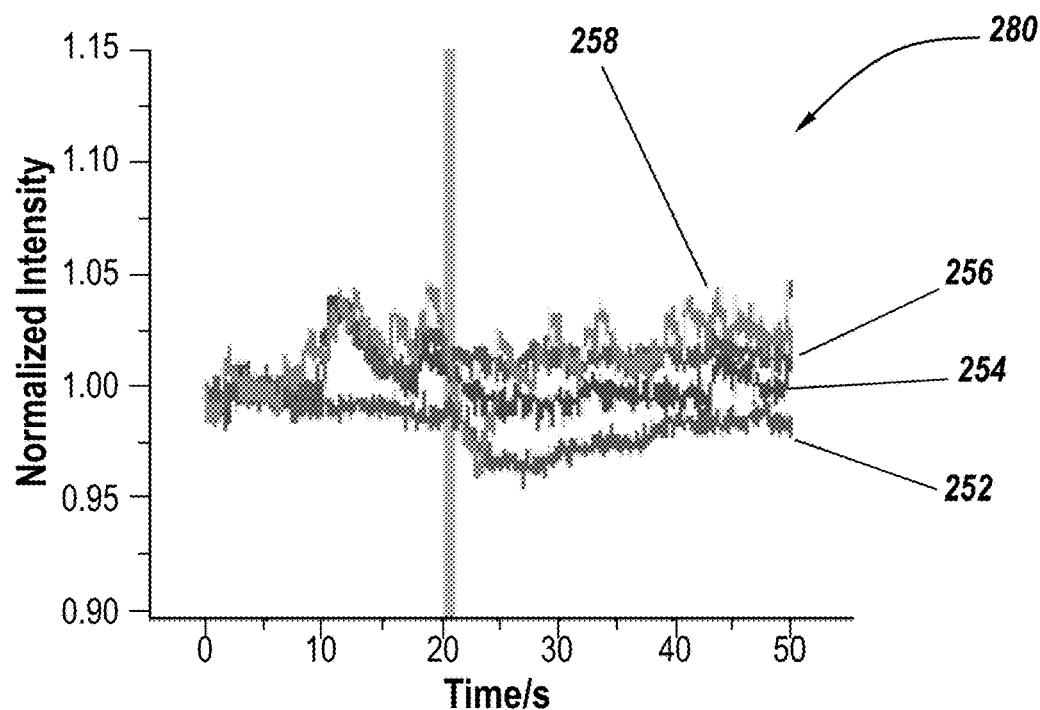
Figure 2I:
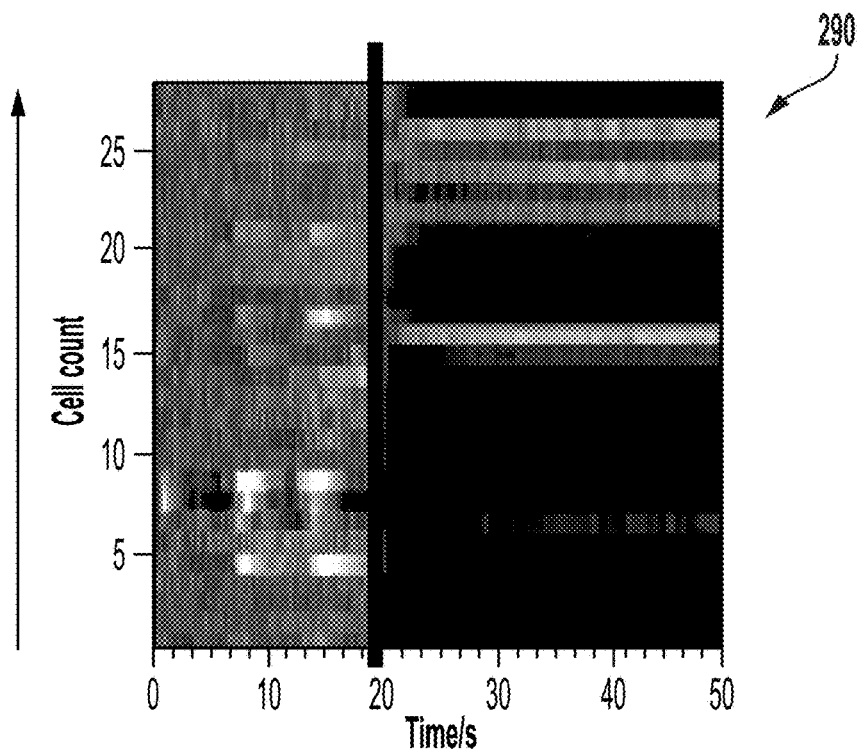
Figure 2J:
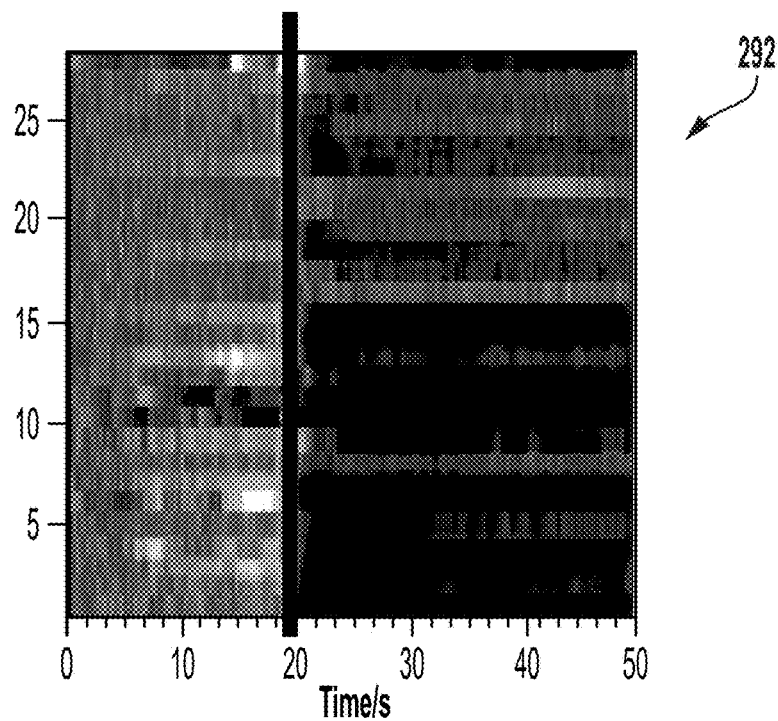
Figure 2K:
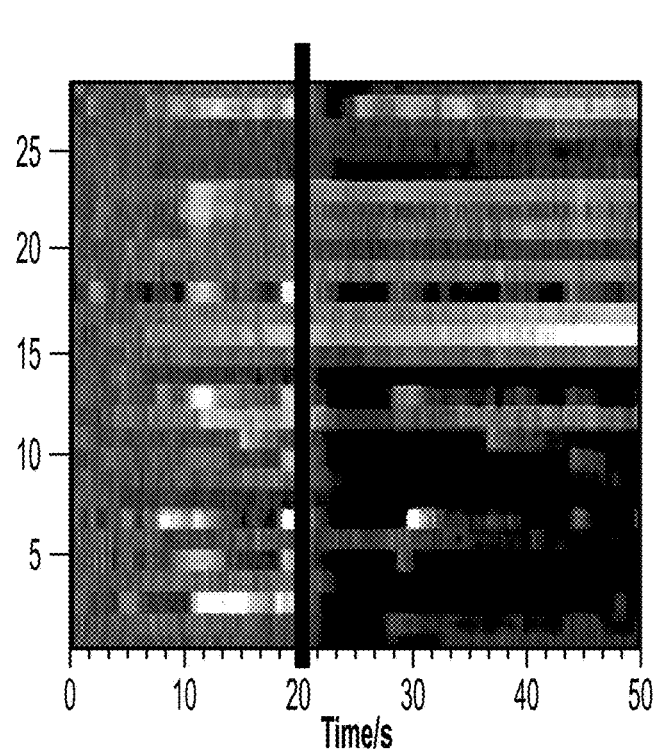
Figure 2L:
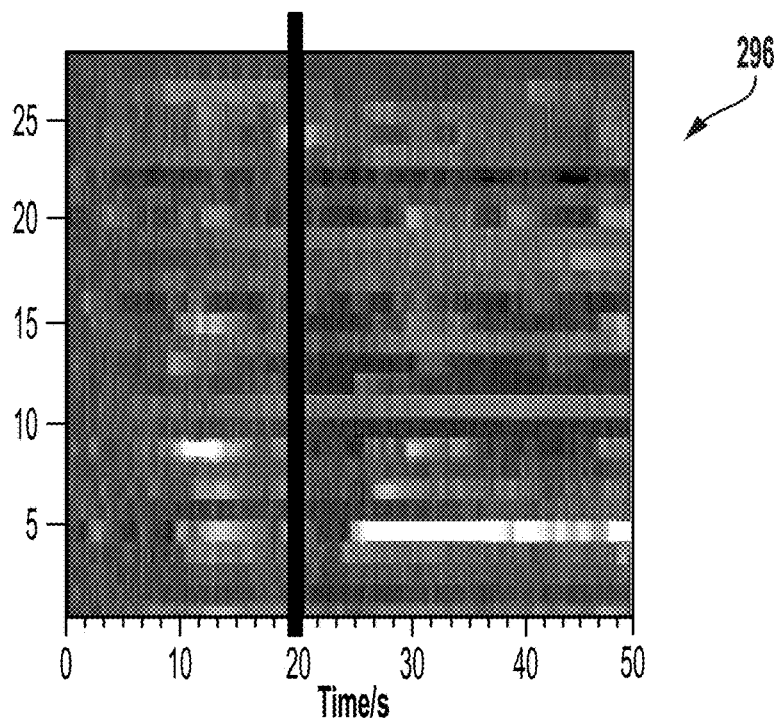
Figure 2M:
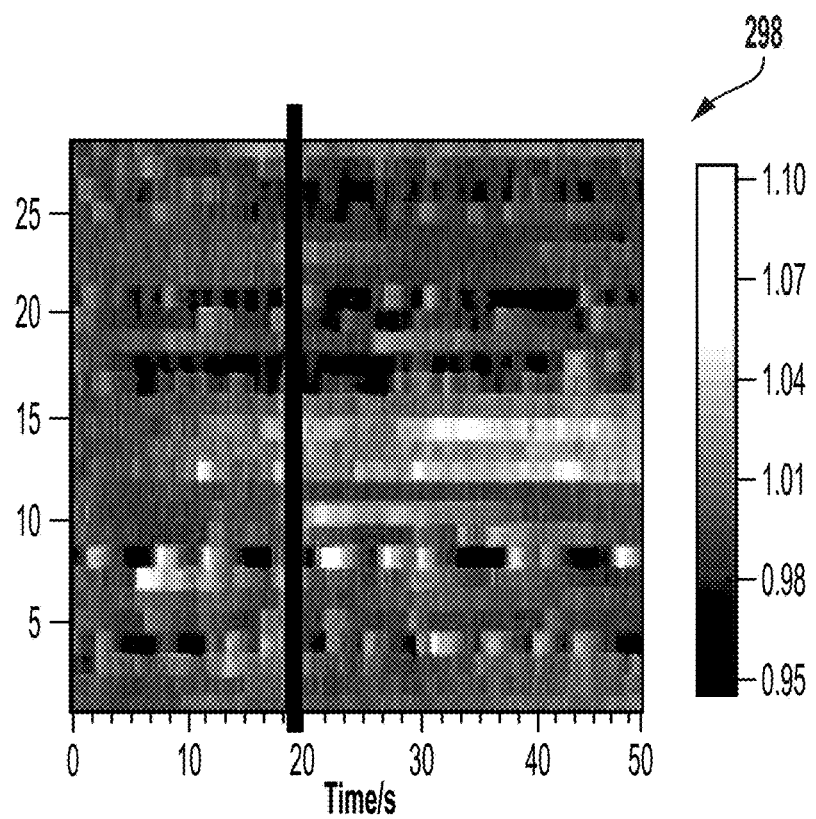
Figure 4:
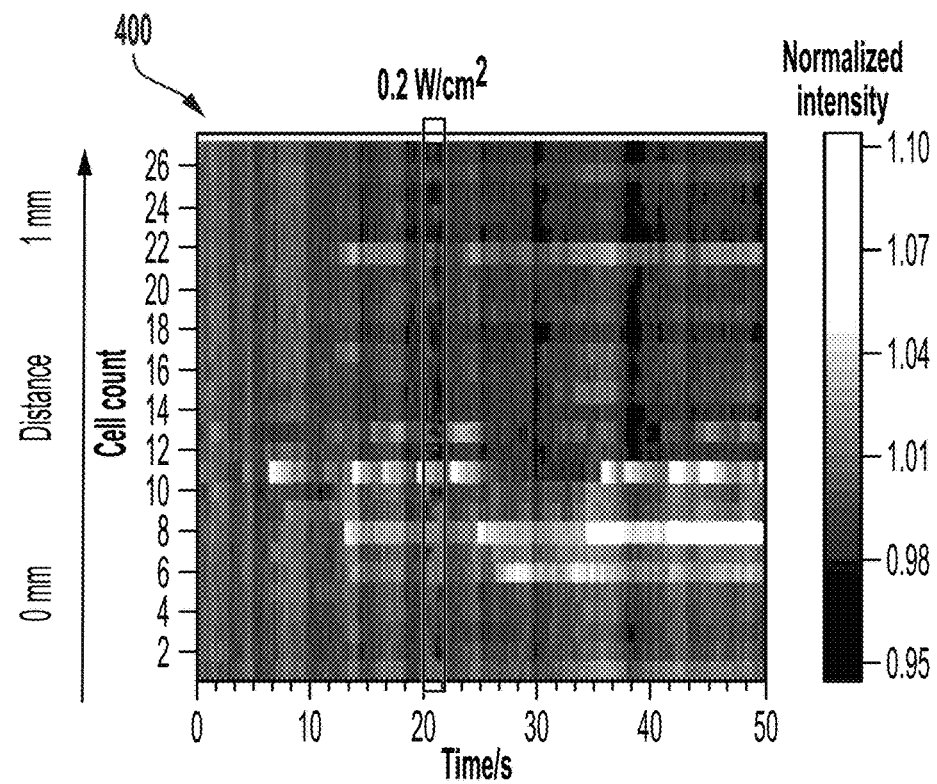
FIG. 4 is a GCaMP fluorescence heatmap showing SRR does not induce inhibition at off resonance frequency.

According to the embodiments of the present disclosure, microwave SRR inhibits neurons with improved efficiency and submillimeter spatial precision. In presenting how the SRR could enhance the efficiency and spatial precision of the MW inhibition according to the present disclosure, the SRR can be submerged in the culture medium above the primary cortical neurons with the gap ~100 µm from the cells. FIG. 2D provides schematic 340 of in vitro experiments with SRR. The SRR can be oriented perpendicular to the culture dish and MW can be delivered with H field perpendicular to the SRR plane. According to the present embodiment, the SRR can then be irradiated with 0.2 W/cm² MW at 2.0 GHz for 1 s. Time-lapse imaging of GCamp6f was implemented to monitor the neural activity is shown in view 250 of FIG. 2E at sites 252, 254, 256, and 258. Average fluorescence traces for 3 regions within the SRR gap is presented in view 260 of FIG. 2F, ~200 µm from the gap at view 270 in FIG. 2G, and ~600 µm from the gap at view 280 in FIG. 2H indicate that the SRR confines the effects of MW inhibition to ~200 µm. Thus, the SRR enables neuronal inhibition with submillimeter spatial precision. As shown in FIG. 4 at view 400, no inhibition was observed at off-resonance frequencies of 1.2 Ghz. According to the illustrative embodiment, the same MW treatment can be repeated at power densities of 2.0 W/cm² (as shown in view 290 in FIG. 2I), 1.0 W/cm² (as shown in view 292 in FIG. 2J), 0.2 W/cm² (as shown in view 294 in FIG. 2K), and 0.02 W/cm² (as shown in view 296 in FIG. 2L), each presented as GCaMP calcium traces for single neurons at varying distances fluorescence heatmap for neurons near the SRR gap at 2.0 GHz for 3 s at varying powers, with cells arranged by distance from SRR gap. The inhibition efficiencies were found to be 9.2%, 6.6%, 2.9%, and 0%, respectively. The strength of the inhibition and the radius of the affected area demonstrate a dependence on power density. Significant inhibition by the SRR was observed at power densities as low as 0.04 W/cm$^2$. In comparison, as shown in the GCaMP fluorescence heatmap view 298 of FIG. 2M, 0.2 W/cm$^2$ MW treatment without the SRR induces no significant neural inhibition, which confirms that the SRR increases the efficiency of neuronal inhibition. Together, these findings demonstrate that the SRR can inhibit neuronal activity with an improved efficiency and spatial precision over MW alone, enabling much lower MW dosage.

Figure 5A:
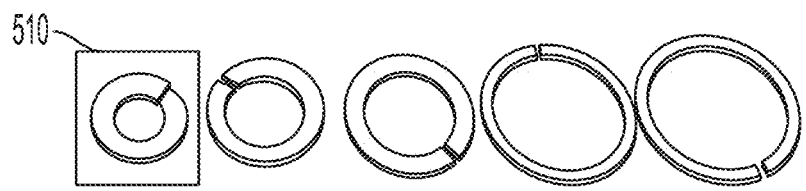
FIG. 5A is an image of differing TiSRR sizes.
Figure 5B:
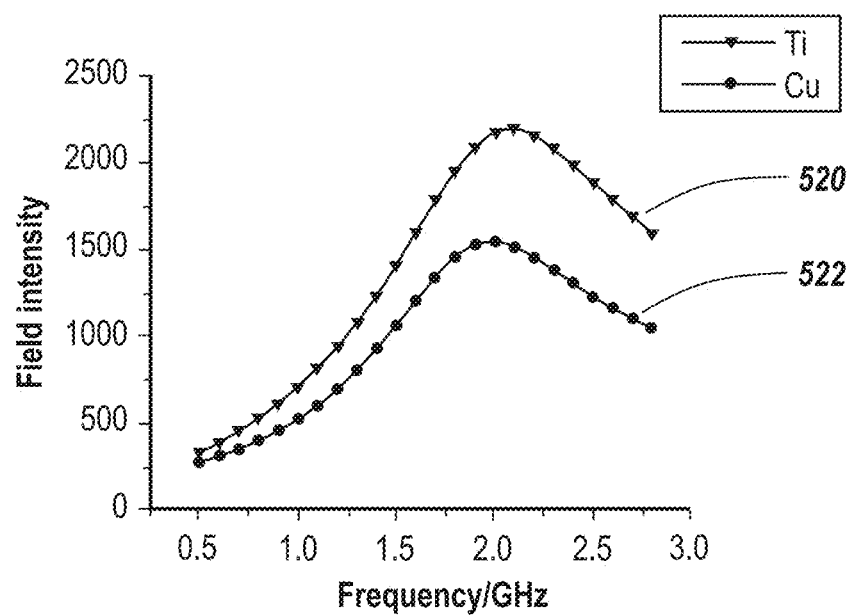
FIG. 5B is a graph comparing TiSRR with a copper SRR.
Figure 5C:
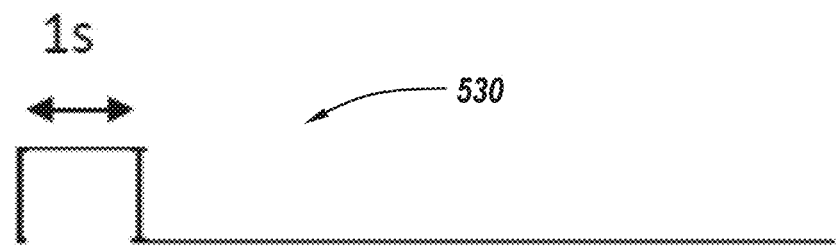
FIG. 5C is a diagram illustrating overall MW dosage is equivalent to the 1 s continuous MW.
Figure 5D:
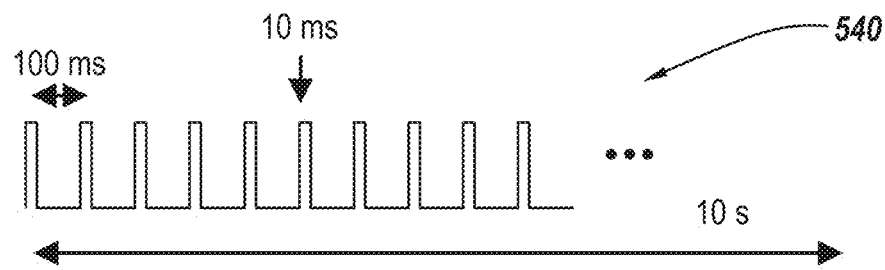
FIG. 5D is a diagram illustrating modulating the microwave to generate a pulse train.
Figure 5E:
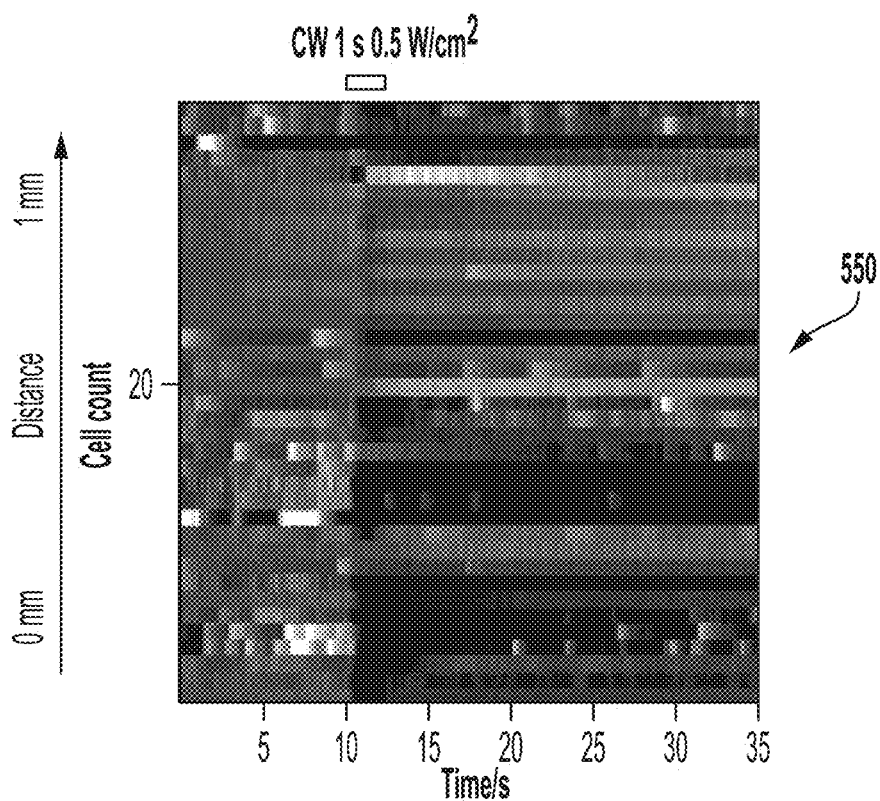
FIGS. 5E-5F are GCaMP fluorescence heatmaps of the continuous and pulsed MW performance compared by irradiating primary cortical neurons with 0.5 W/cm2 at 2.1 GHz in the presence of the TiSRR.
Figure 6:
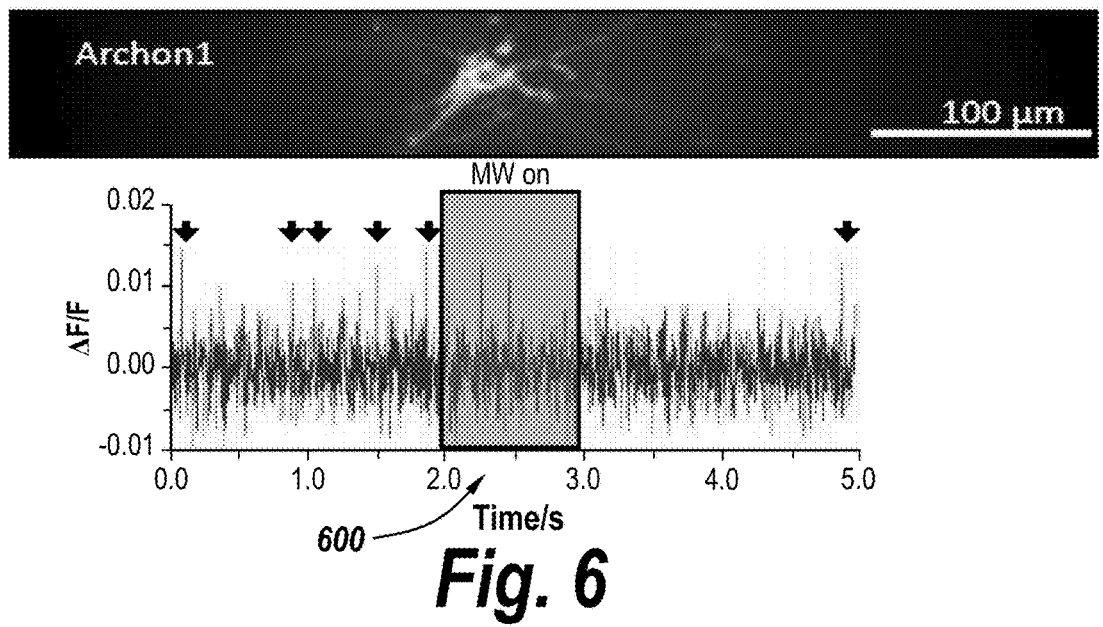
FIG. 6 shows an image and chart of voltage imaging with TiSRR inhibition.

According to the embodiments of the present disclosure, biocompatible titanium SRR inhibits neurons with sub-millimeter spatial precision. Although the copper SRR has shown neuronal inhibition with enhanced efficiency and spatial precision, the poor compatibility of copper with tissue hinders its capability in biomedical application. Titanium alloy, on the other hand, has shown excellent biocompatibility with tissue and has seen wide application as tissue implants in the clinics such as artificial joints and pacemakers. To demonstrate that a titanium alloy is a better candidate for in vivo application, a titanium SRR (TiSRR) with outer diameter 2.14 mm, gap 0.3 mm, height 0.2 mm and width 0.27 mm can be fabricated, as presented at ring 510 in FIG. 5A. For example, the TiSRR can be fabricated from a titanium alloy tube sectioned with electron discharge machining. To verify that the TiSRR has a similar resonance effect as the copper SRR, finite element modeling can be performed, and are modeled at Ti graph line 520 and Cu graph line 522 in FIG. 5B. As shown in FIG. 5B, the TiSRR generates ~37% greater MW field at the ring gap than that of the copper SRR, likely due to its geometry. The efficiency of neural inhibition with TiSRR was tested by the same setup as described in FIG. 2D. MW irradiation of primary cortical neurons with 0.5 W/cm$^2$ MW at 2.1 GHz for 1 s demonstrates that the TiSRR achieves 38.9% inhibition in vitro as presented in GCaMP fluorescence heatmap view 550 of FIG. 5E and FIG. 6, which demonstrates voltage imaging with TiSRR inhibition at highlighted column view 600. Further, voltage fluorescence imaging of primary cortical neurons transfected with Archon can confirm that these effects were not artifacts of thermal interference with the GCaMP6f fluorescence.

Figure 5F:
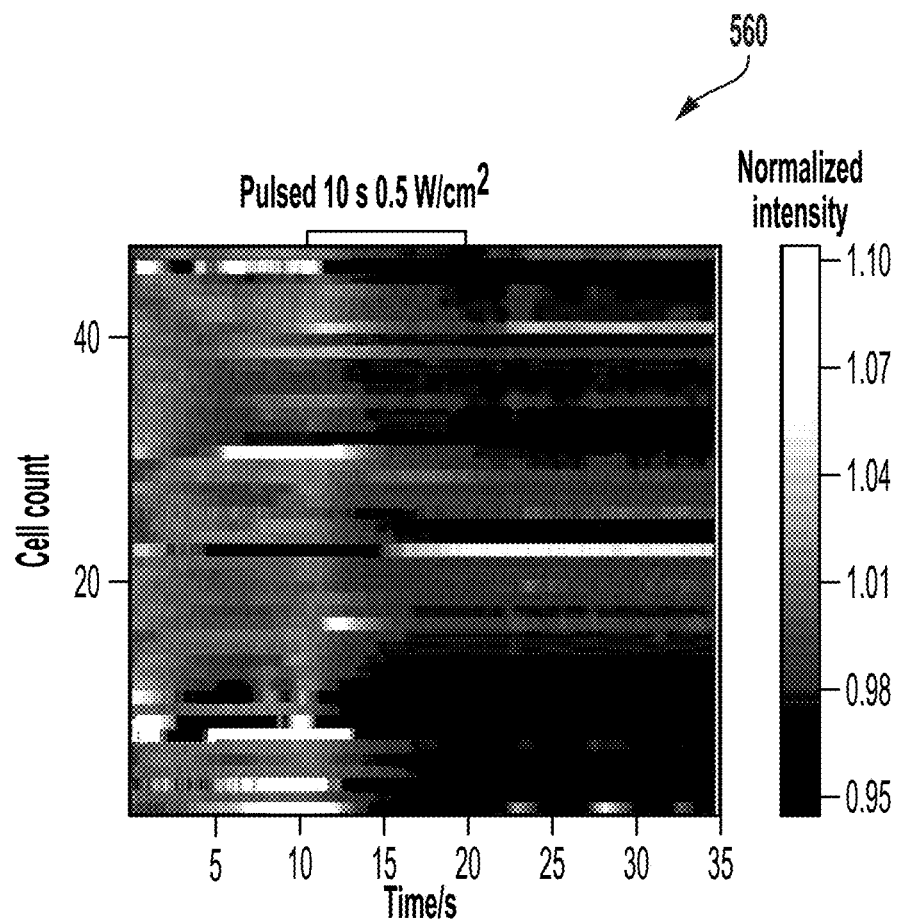
Figure 5G:
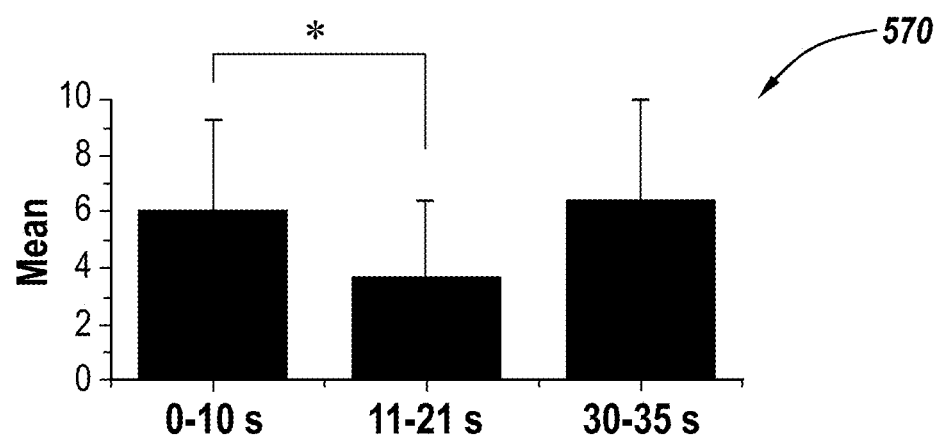
FIGS. 5G-5H are trace views showing continuous wave and pulsed wave inhibition efficiencies when irradiating primary cortical neurons.
Figure 5H:
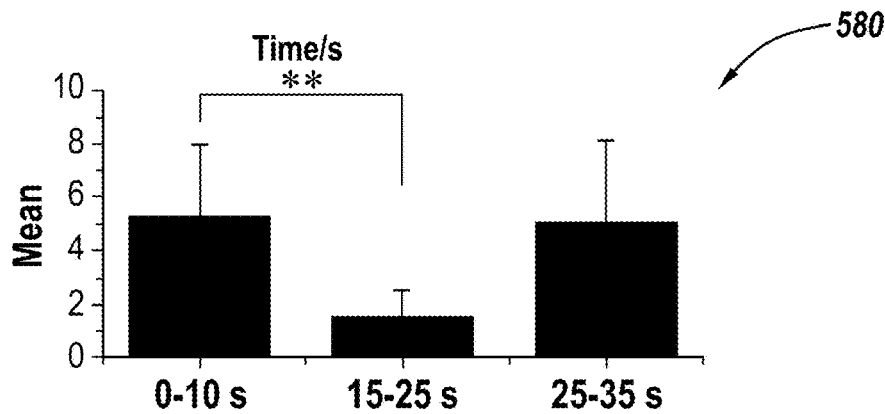
Figure 5I:
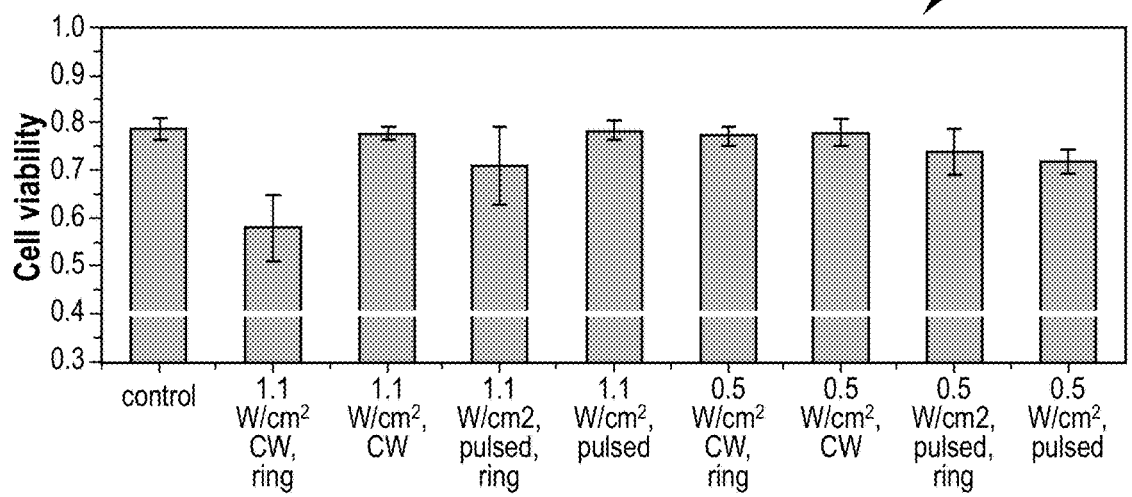
FIG. 5I is a trace view of cell viability measured after MW treatment with 3.2 W/cm² and 1.3 W/cm², with or without the TiSRR, and under continuous or pulsed MW.
Figure 7:
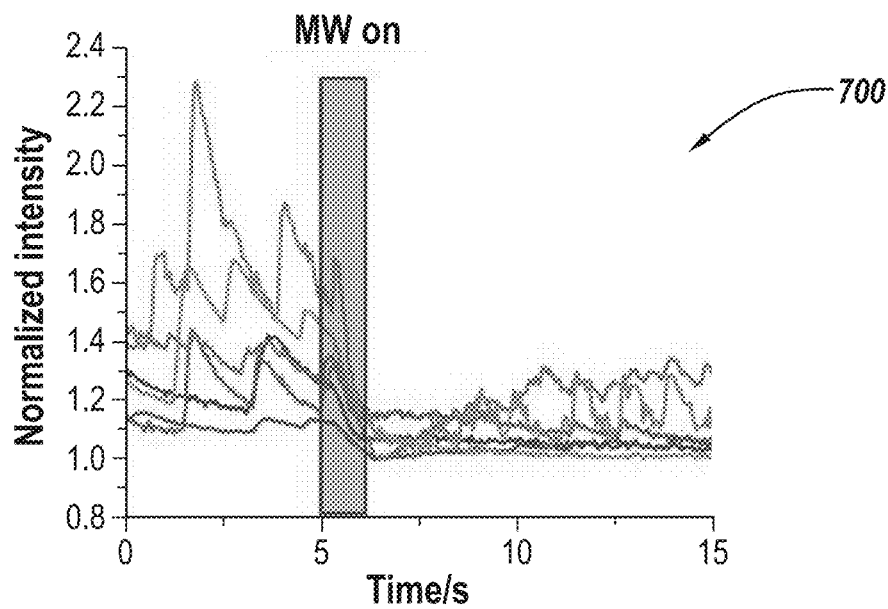
FIG. 7 is a graph showing calcium traces for TiSRR.

For clinical applications, it may be preferable to prolong the MW inhibition without increasing the thermal accumulation or MW dosage. To this end, the present disclosure includes modulating the microwave to generate a pulse train having a 10% duty cycle over 10 s, i.e. 10 ms pulse width with 100 Hz repetition rate, as shown in view 540 of FIG. 5D. The overall MW dosage is equivalent to the 1 s continuous MW, as shown in view 530 of FIG. 5C. As shown in GCaMP fluorescence heatmaps view 550 of FIG. 5E and 560 of FIG. 5F, the continuous and pulsed MW performance can be compared by irradiating primary cortical neurons with 0.5 W/cm$^2$ at 2.1 GHz in the presence of the TiSRR. The continuous wave and pulsed wave had inhibition efficiencies of 38.9% and 100%, respectively in trace views 570 and 580 of FIGS. 5G and 5H, respectively. Cell viability can be measured after MW treatment with 3.2 W/cm$^2$ and 1.3 W/cm$^2$, with or without the TiSRR, and under continuous or pulsed MW, as shown in trace view 590 of FIG. 5I and in graph view 700 of FIG. 7, showing single cell traces for the neurons presented in view 590 of FIG. 5I and in graph view 700 of FIG. 7, showing single cell traces for the neurons presented in view 590 of FIG. 5I. In the case of 3.2 W/cm$^2$ with TiSRR, the pulsed MW have greater cell viability. Taken together, according to the present disclosure, these results indicate that the TiSRR provides a platform for neuronal inhibition with comparable performance to the copper SRR and greater biocompatibility. Furthermore, pulse modification is a viable method for prolonging MW treatment without inducing thermal toxicity.

Figure 8A:
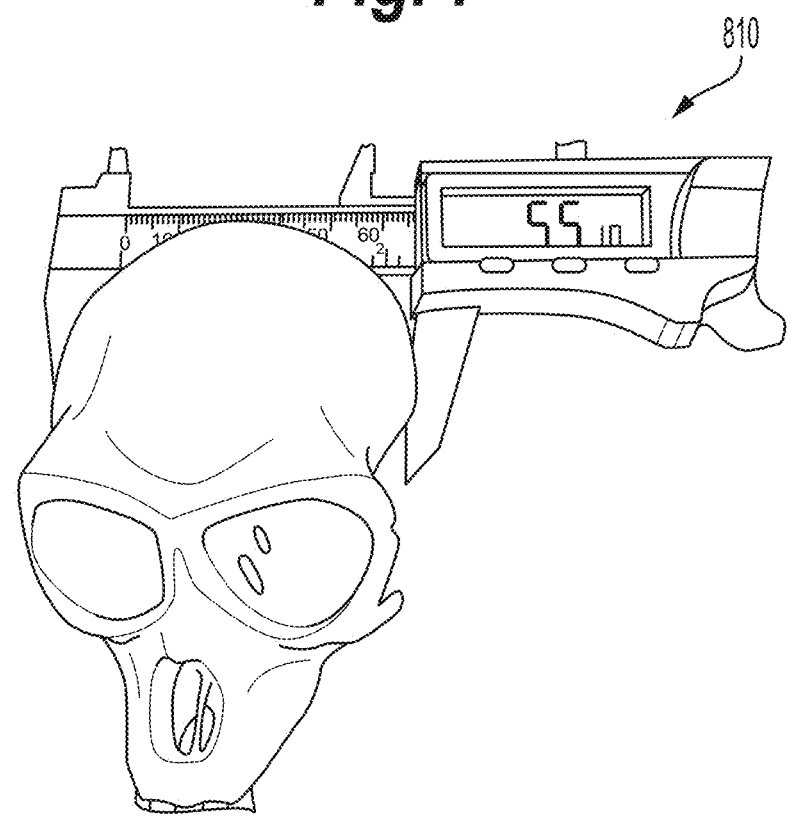
FIG. 8A is a front view of a macaque monkey skull inside the MW waveguide used for transcranial inhibition.
Figure 8B:
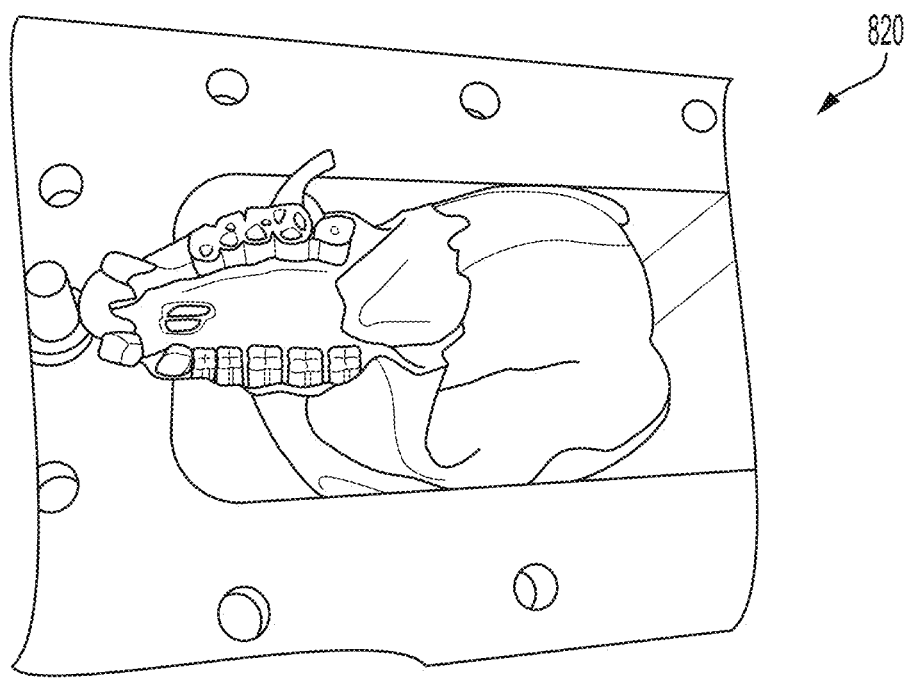
FIG. 8B is a bottom view of a macaque monkey skull inside the MW waveguide used for transcranial inhibition.
Figure 8C:
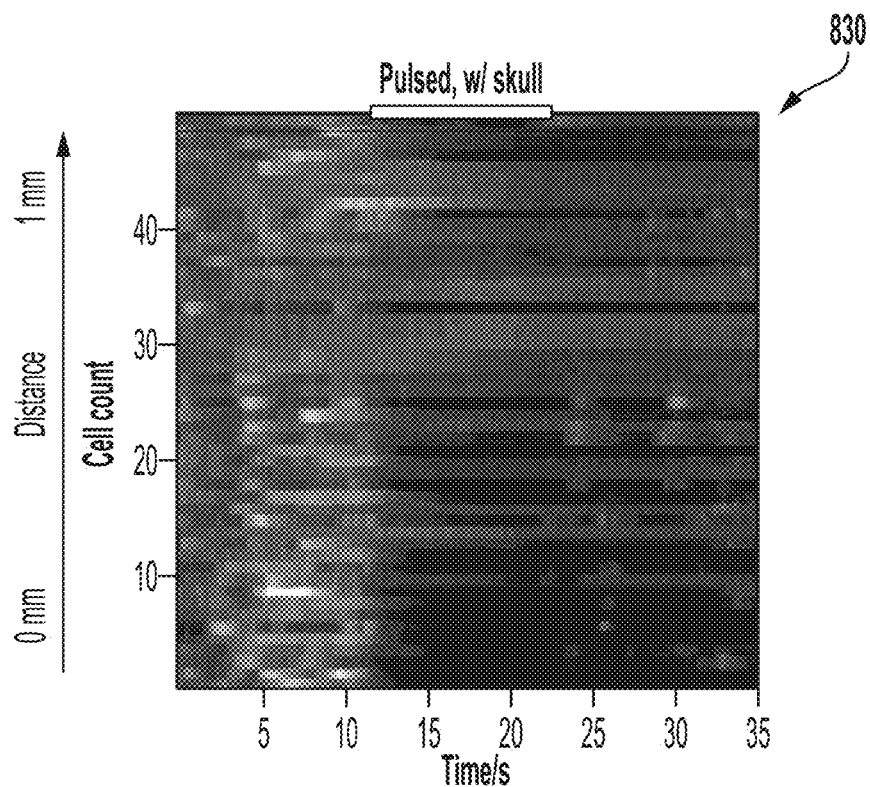
FIG. 8C is a GCaMP fluorescence heatmap for neurons near the TiSRR gap under 0.2 W/cm² pulsed MW irradiation at 2.1 GHz with the monkey skull.
Figure 8D:
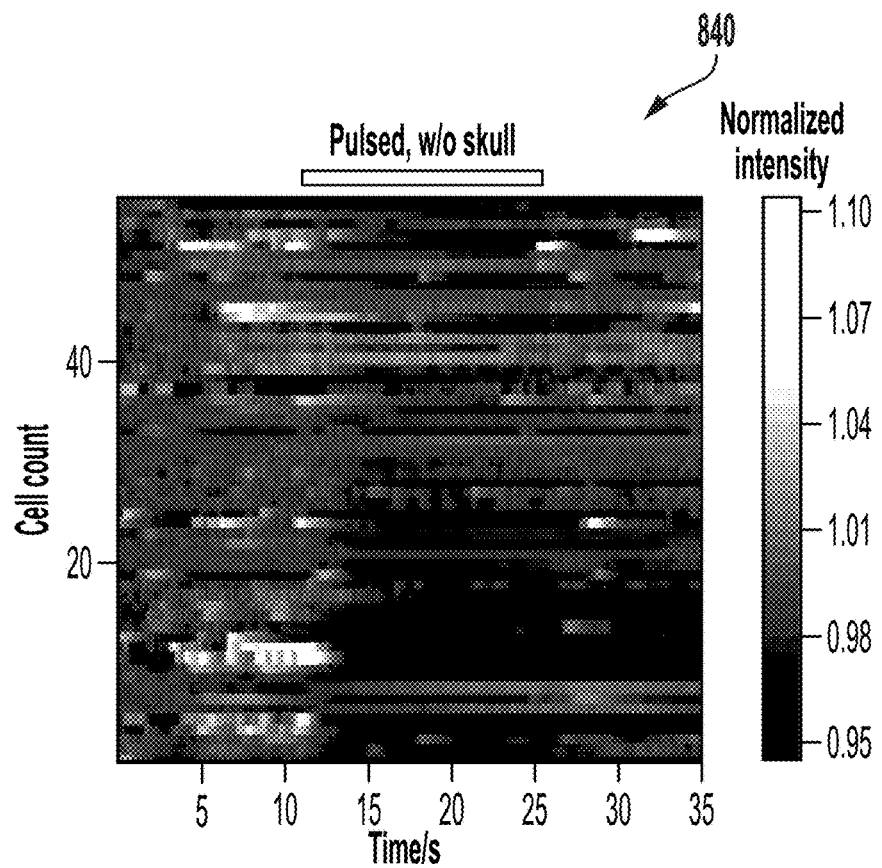
FIG. 8D is a GCaMP fluorescence heatmap for neurons near the TiSRR gap under 0.2 W/cm² pulsed MW irradiation at 2.1 GHz without the monkey skull.
Figure 8E:
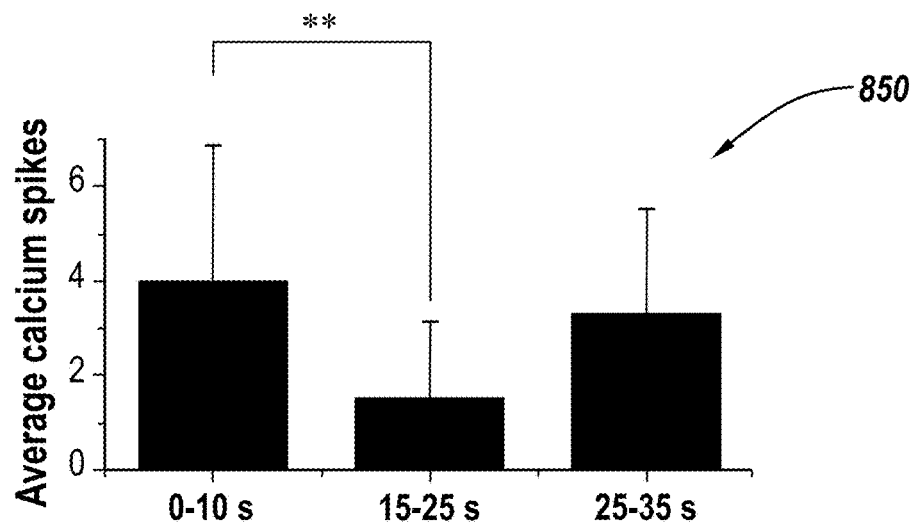
FIG. 8E is a trace view of average calcium spikes for neurons near the TiSRR gap under 0.2 W/cm² pulsed MW irradiation at 2.1 GHz with the monkey skull.
Figure 8F:
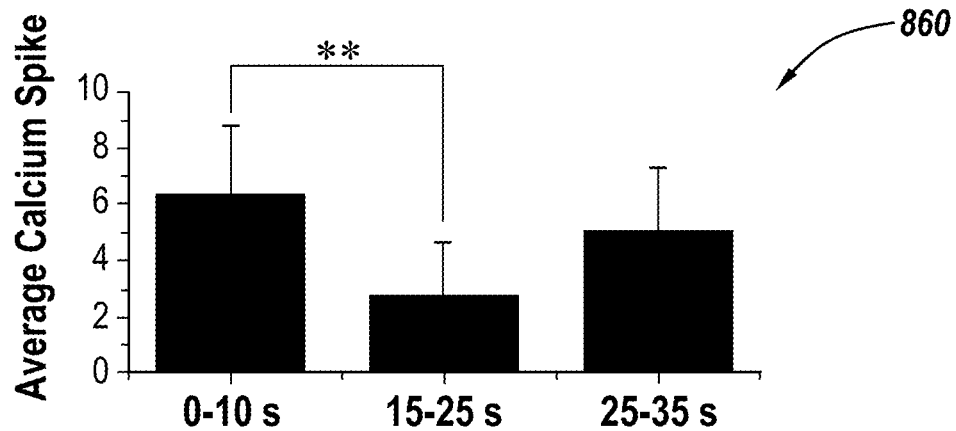
FIG. 8F is a trace view of average calcium spikes for neurons near the TiSRR gap under 0.2 W/cm² pulsed MW irradiation at 2.1 GHz without the monkey skull.

According to the embodiments of the present disclosure, TiSRR mediates transcranial inhibition of neurons. An illustrative application of the present disclosure includes being able to achieve wireless neuronal inhibition for the treatment of disorders like epilepsy. For the device to be wireless, MW must be delivered from outside the skull to the implanted SRR. The mm-scale wavelength of MW allows for deep penetration into biological tissue, including bone. MW has been demonstrated to penetrate >50 mm into the human skull while maintaining over 50% of its energy, making wireless transcranial MW inhibition feasible. To demonstrate the potential transcranial inhibition capabilities of the MW TiSRR, in FIGS. 8A and 8B, a macaque monkey skull with ~3 mm thickness can be placed inside the MW waveguide, as shown in views 810 and 820, respectively. The TiSRR can be placed over primary cortical neurons and irradiated with 0.5 W/cm$^2$ pulsed MW at 2.1 GHz for 10 s, as shown in GCaMP fluorescence heatmaps for neurons near the TiSRR gap at view 830 of FIG. 8C, which is pulsed with the skull, and view 840 of FIG. 8D, which is pulsed without the presence of the skull. With the skull, as shown at view 850 of FIG. 8E, the TiSRR achieved 14.7% inhibition, while without the skull, as shown at view 860 of FIG. 8F, 63.1% inhibition can be achieved. This illustrative example thereby demonstrates the capability of the TiSRR to perform transcranial neuronal inhibition for wireless application of the device.

Figure 9A:
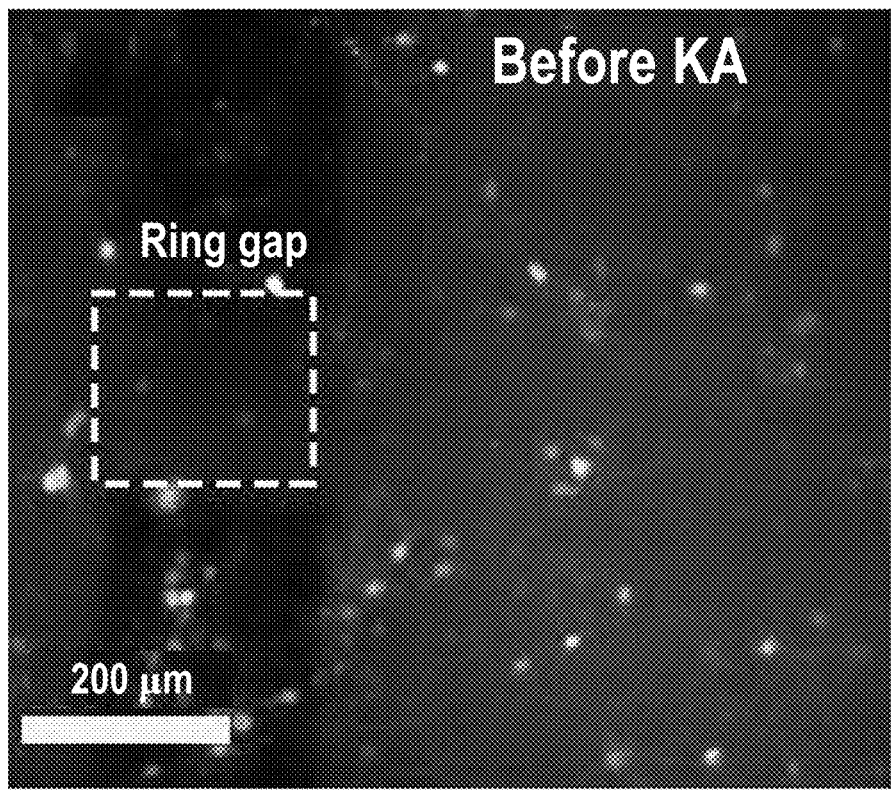
FIG. 9A shows a before GCaMP florescence image of neurons before treatment with kainic acid.
Figure 9B:
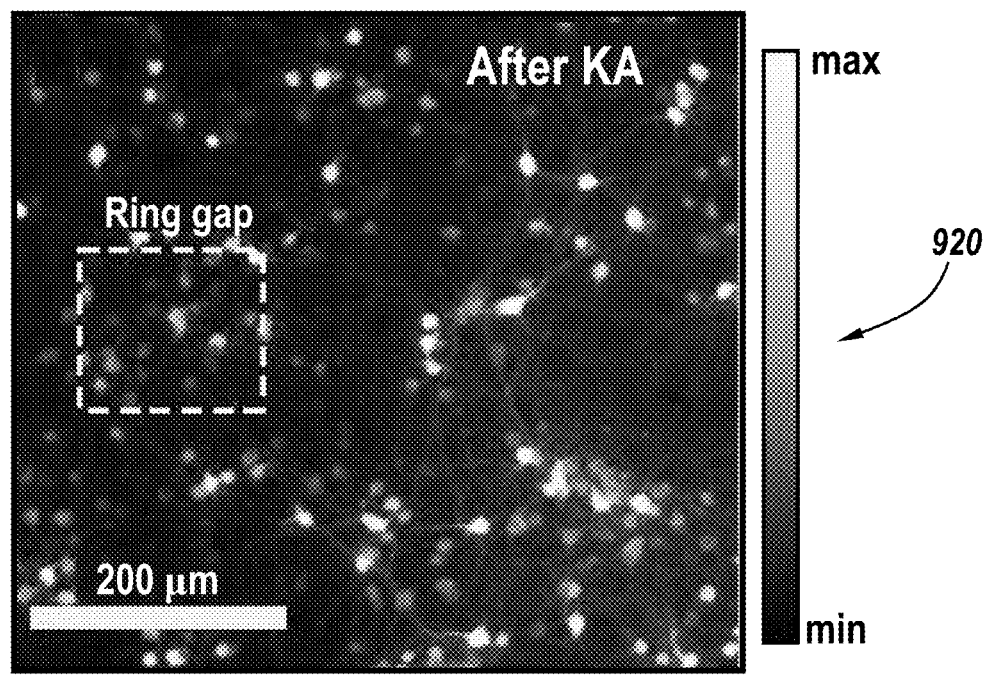
FIG. 9B shows an after GCaMP florescence image of neurons following treatment with kainic acid.
Figure 9C:
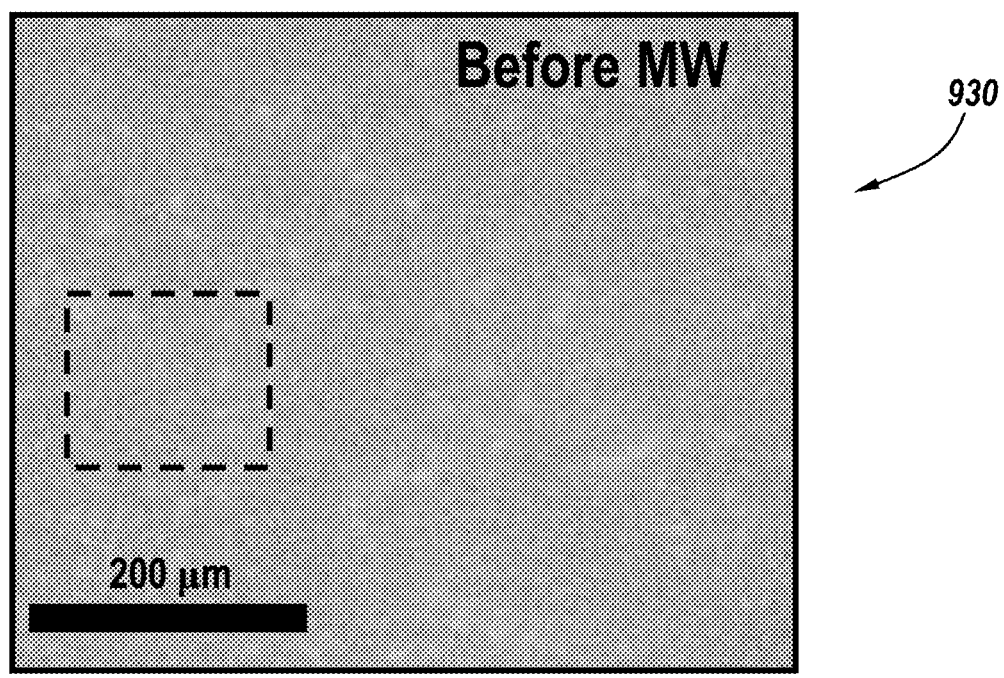
FIG. 9C shows a before GCaMP florescence image of neurons before treatment with pulsed MW.
Figure 9D:
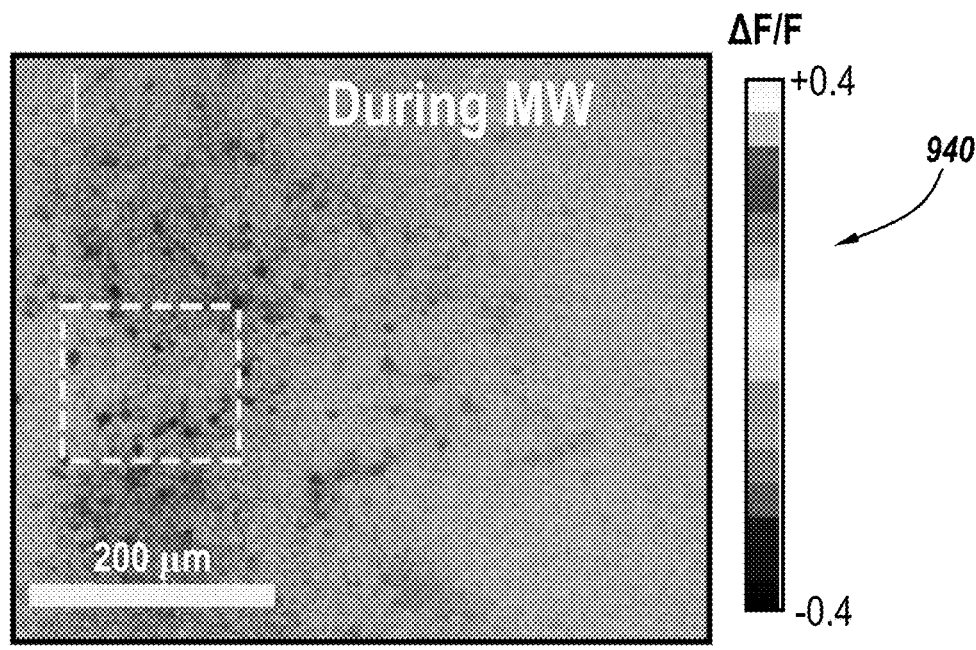
FIG. 9D shows a present GCaMP florescence image of neurons during treatment with pulsed MW.
Figure 9E:
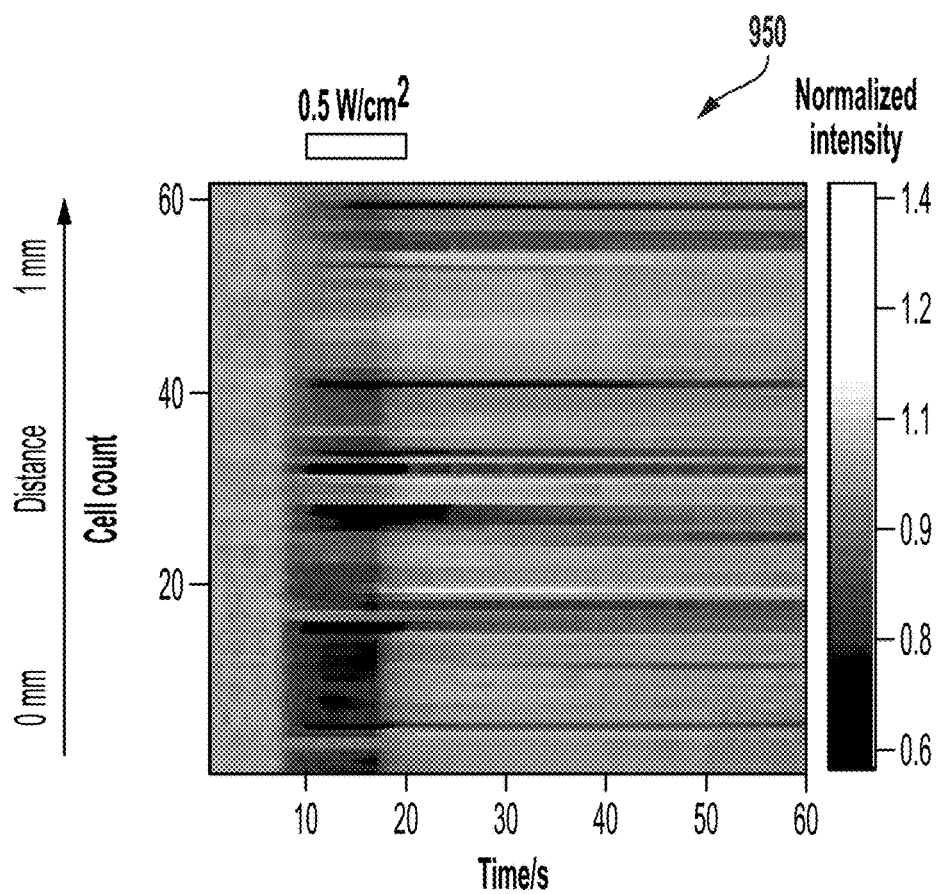
FIG. 9E is a GCaMP fluorescence heatmap of kainic acid-induced activity suppressed by 0.5 W/cm² pulsed MW at 2.1 GHz for 10 s.
Figure 9F:
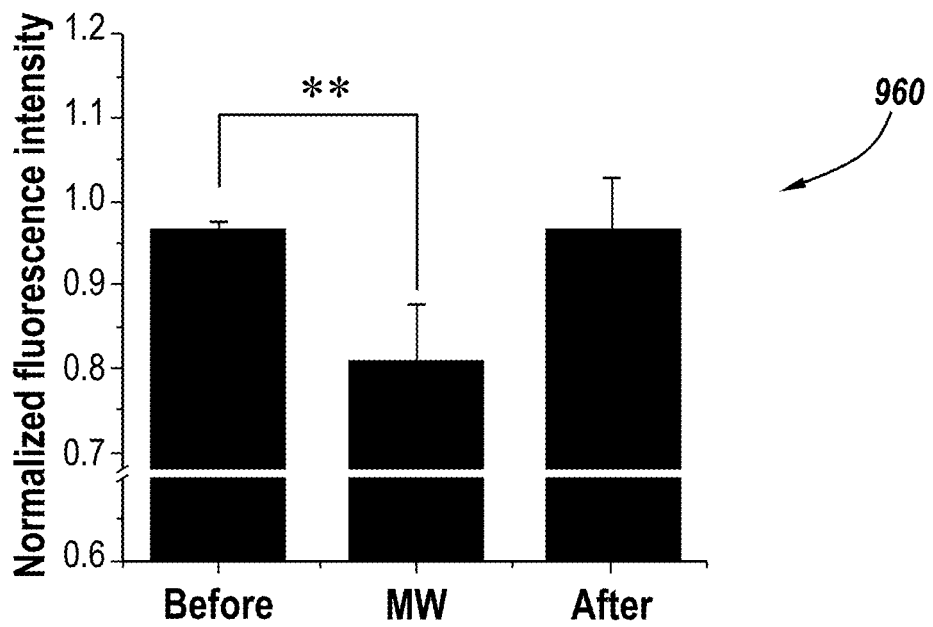
FIG. 9F is a trace view of normalized fluorescence intensity before, during, and after MW treatment.

According to the embodiments of the present disclosure, TiSRR can inhibit stimulated neurons as well. Traditionally, epileptic seizures are characterized by excessive neuronal excitability. The kainic acid (KA) mouse model of epilepsy is commonly used to study the disorder. KA is an analog of glutamate that acts as an agonist to kainite receptors, and in small doses, KA increases excitability of a cell population. When injected intracerebrally or systemically, KA evokes acute as well as chronic seizures. According to the present disclosure, to demonstrate the ability of the TiSRR to inhibit KA-induced activity, 20 mM KA in DMSO can be added to primary cortical neurons. FIG. 9A shows a before GCaMP florescence image 910 of neurons before treatment with kainic acid, and FIG. 9B shows an after GCaMP florescence image 920 of neurons following treatment with kainic acid. Treatment with KA noticeably increased the fluorescence intensity. Additionally, the TiSRR can be placed over the neurons and irradiated with 0.5 W/cm$^2$ pulsed MW at 2.1 GHz for 10 s; FIG. 9C shows a before GCaMP florescence image 930 of neurons before treatment with pulsed MW, and FIG. 9D shows a present GCaMP florescence image 940 of neurons during treatment with pulsed MW. As shown in view 960 of FIG. 9F, neuronal inhibition is evident, with an efficiency of 16.3%. For most cells, inhibition only occurred during MW irradiation, but for some, the effect is longer lasting, as presented in view 950 of FIG. 9E. The inhibitory effect was confined to ~200 μm from the SRR gap for FIG. 9D, further demonstrating the spatial precision of the SRR. These results indicate that the TiSRR can inhibit a stimulated increase in neuronal activity with high spatial precision.

Figure 10A:
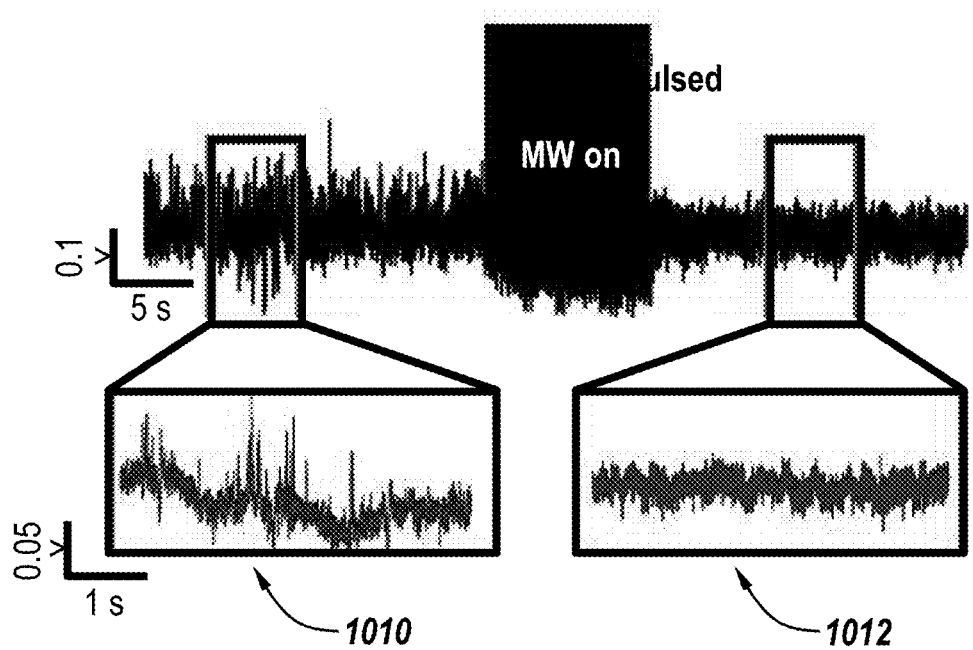
FIG. 10A is a diagram showing effective suppression of seizure activities in vivo recorded via EMG can be observed before and after.
Figure 10B:
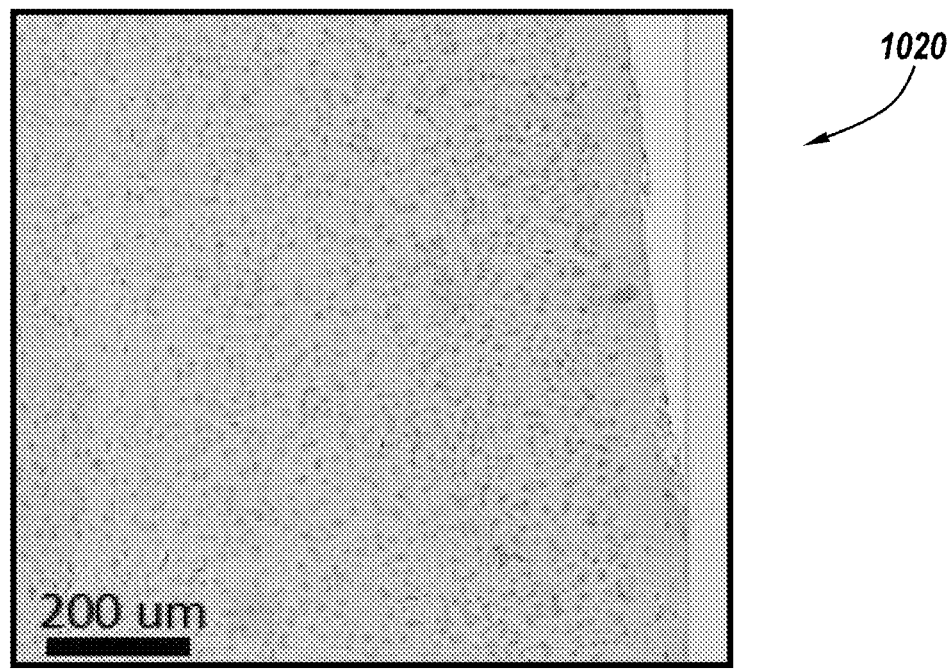
FIG. 10B is a histology image of tissue after exposure to TiSRR to treat epilepsy in a mouse subject.
Figure 11A:
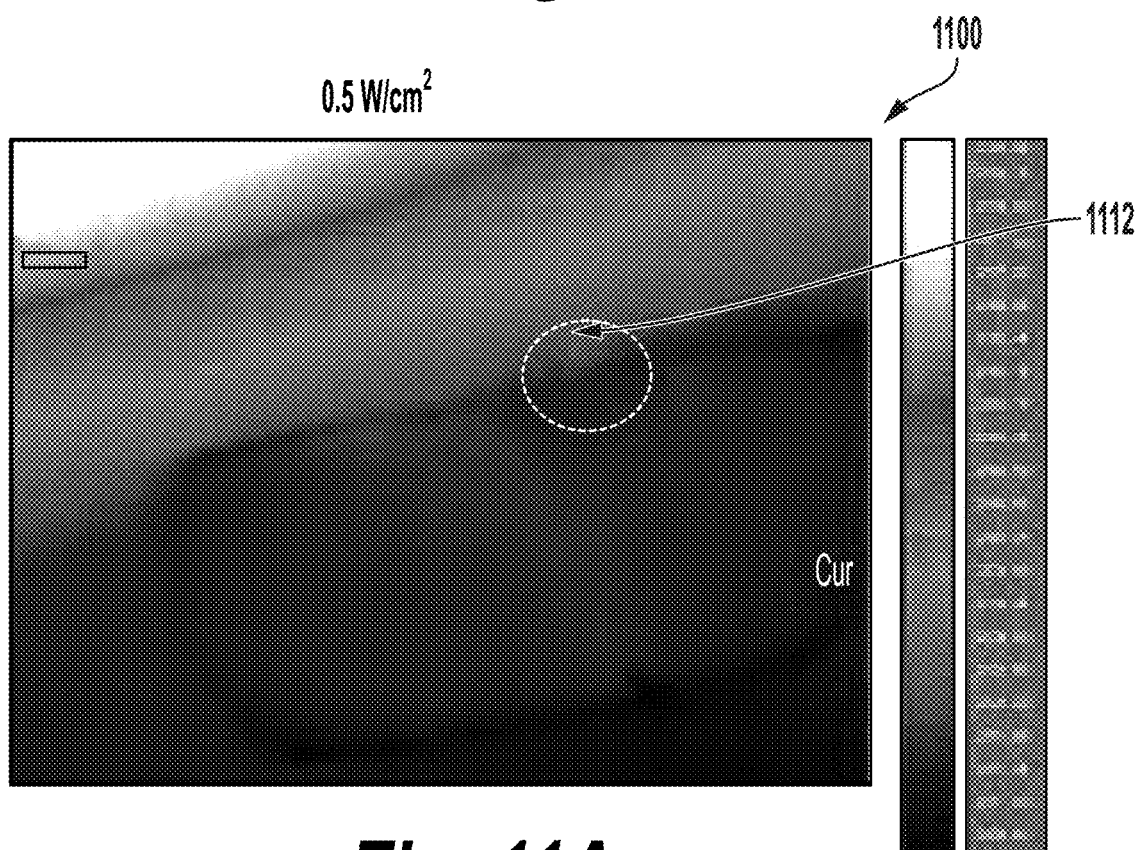
FIG. 11A is a thermal image of an SRR measurement.

According to the embodiments of the present disclosure, TiSRR suppresses seizures in mouse model of epilepsy without tissue damage. To demonstrate by way of illustrative example, the present disclosure provides a mouse model of epilepsy, induced by intracortical injection of picrotoxin. By applying pulsed microwave via the SRR, effective suppression of seizure activities in vivo recorded via EMG can be observed before and after at views 1010 and 1012 respectively in FIG. 10A. Independently, a mouse brain was repeatedly exposed to pulsed MW. Thermal measurement of the SRR showed <1.5° C. increase at the gap, as shown in view 1100 of FIG. 11A at site 1112 and at temporal plot line 1114 in graph 1120 of FIG. 11B. Histology of the cortical tissue was performed at the BU Histopathology Lab. The histology appeared normal, as shown at 1020 of FIG. 10B, indicating in vivo safety for treatment in line with the present disclosure.

The embodiments of the present disclosure offer the first application of a microwave split-ring resonator for wireless neuromodulation at sub-millimeter precision. Microwave has not previously been used to modulate neurons in vivo because at high powers it can cause thermal damage. As shown in the previous applications, by implanting an SRR in the deep brain, microwave inhibition efficiency is much improved and dosages below the safe exposure limit can be used. Wirelessly powered neural implants have received great attention in recent years, as these implants possess clear advantages over tethered devices in that they reduce tissue damage during surgical procedures and, subsequently, diminish infection in daily use. However, a primary challenge for wireless neural stimulators is to create efficient miniature devices that operate at deep tissue. For efficient wireless power transfer, antennas need to have sizes comparable to the electromagnetic wavelength. Currently, the majority of miniaturized wireless neural modulators work in the MHz range and require a surface-level receiver to couple with the waves reach the deep brain, increasing the invasiveness and size of the implant. For fully internalized devices, power delivery becomes difficult due to their small size, thus limiting the depth of the implants. More recently, ultrasound-powered neural modulators have enabled effective power transfer at several centimeters deep into the tissue. Such devices, however, are difficult to operate in free moving animals due to the impedance mismatch between air and soft tissue, thus requiring direct contact and application of ultrasonic gel.

Figures 11B, 12:
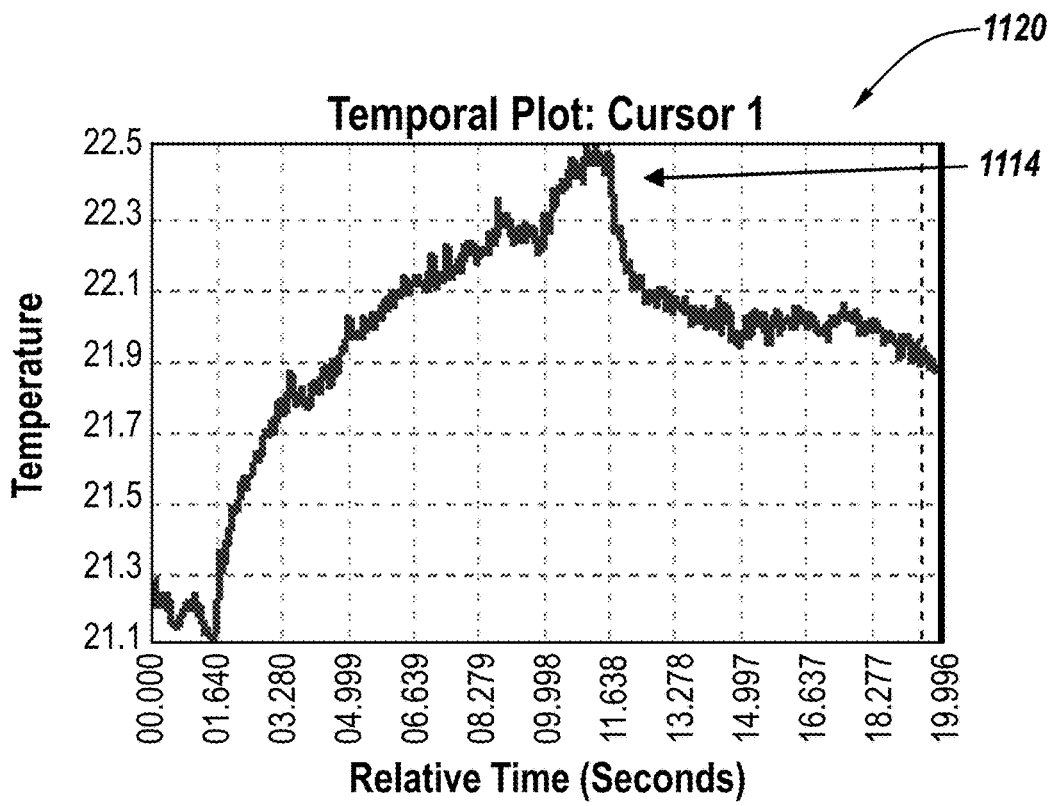
FIG. 11B is a graph of the plotline relating to the SRR measurement of FIG. 11A.
FIG. 12 is a table comparing microwave SRR with other existing neuromodulation implants.

Compared to other devices, the SRR of the present disclosure offers several unique advantages, as shown in table 1200 of FIG. 12, which provides a comparison of microwave SRR with existing neuromodulation implants. According to one implementation, the SRR of the present disclosure creates a microwave field with ultrahigh spatial precision on the order of 100 μm, which is one-hundredth the wavelength of microwave. This precision enables region-specific brain modulation or selective inhibition of a single nerve. According to one implementation, the implantable, miniaturized SRR has a volume of 1.8 mm$^3$, which makes it the smallest implant for wireless modulation. This small size greatly reduces invasiveness and minimizes the wound healing response. According to one implementation, the SRR allows wireless neural inhibition at centimeter-scale depths. This capability enables deep-tissue modulation for the treatment of disorders involving excessive excitability, such as neuropathic pain.

A major innovation of the SRR of the present disclosure is that it allows the use of microwave dosages within the safety limits established by IEEE. The threshold for safe RF exposure is 10 W/kg averaged over 6 minutes, which corresponds to an average dosage of 3600 J/kg. Each treatment, consisting of 10 s pulsed MW at 0.5 W/cm$^2$, corresponds to 500 J/kg in vitro (17.5 mm radius, 5 mm depth). This means up to 7 sessions of treatment can be administered within 6 minutes according to IEEE standards. The dosage of the present disclosure is also below those used in previous literature. Furthermore, the major mechanism behind MW toxicity is thermal damage to the blood brain barrier (BBB). Studies have found that the dog brain could withstand temperatures up to 42° C. for 45 min before irreversible damage to the BBB occurred. Studies in other species—including rats, monkeys, rabbits, and pigs—revealed that most brains could withstand at least 1 min at 43° C. without damage, with pig brains lasting over 150 hours. When placed in bulk PBS and irradiated with 10 s pulsed MW at 0.5 W/cm$^2$, the SRR gap reached a peak of 24° C. (22° C. baseline) when applied according to the present disclosure. Therefore, the present device operates within the safety parameters for MW exposure to the brain.

According to the embodiments of the present disclosure, numerical simulation of the resonance frequency of SRR can include, for example, simulations performed in COMSOL Multiphysics 5.3a. As an illustrative example, the SRR can be placed in bulk PBS medium with electrical conductivity 1.56 S/m and a relative permittivity of 70. The copper SRR can be modeled as a coil with 0 axial offset, outer diameter 2.56 mm, gap 0.2 mm, height 0.2 mm and width 0.03 mm. The titanium SRR can be modelled as a cylinder with outer diameter 2.14 mm, gap 0.3 mm, height 0.2 mm and width 0.27 mm. The MW originates from a 50 cm$^2$ port with a plane wave input that has E polarized in the y-direction. H can be polarized perpendicular to the SRR plane in the z-direction. Scattering conditions can be used at the boundaries of the simulated area.

According to the embodiments of the present disclosure, copper SRR fabrication, or manufacturing, is included. As an illustrative example, the copper SRR can be laser cut from a copper sheet by Kuso-Relock USA LLC. According to the embodiments of the present disclosure, titanium SRR fabrication is disclosed. The TiSRR can be fabricated from a titanium alloy tube with outer diameter tapering from 2 mm to 4 mm. Electrical discharge machining (EDM) wire cutting with a 100-μm diameter wire can be used to create a slit of 200 μm down the length of the tube. Then, multiple parallel cuts can be made every 200 μm perpendicular to the slit to produce SRRs of varying diameters. As an additional illustrative example, manufacturing a split-ring resonator (SRR) more generally can include first coating a surface of a substrate with a lift-off resist (LOR) first layer, coating the LOR first layer with an lithography resist second layer to form a bi-layer, patterning the lithography resist layer, and depositing a metal on the patterned resist later by electron beam deposition to create a patterned metal layer through lift-off process.

According to the embodiments of the present disclosure, cell culturing includes primary cortical neurons harvested from [Sprague-Dawley rats] at embryonic day 18 (E18), for example. As an illustrative example, cortices can be dissected from rats of either sex and digested with papain (0.5 mg/mL in Earle's balanced salt solution) (Thermofisher Scientific). Neurons can be plated onto poly-D-lysine coated glass bottom culture dishes in Dulbecco's Modified Eagle Medium (Thermofisher Scientific) with 10% fetal bovine serum (Thermofisher Scientific). After 24 hours, medium can be replaced with feeding medium consisting of Neurobasal medium supplemented with 2% B-27 (Thermofisher Scientific), 1% N2, and 1% GlutaMAX™ (Thermofisher Scientific). 0.1% 5-fluorodeoxyuridine (FdU) can also be added to remove glial cells. At this time point, neurons can be incubated with 0.1% pAAV.Syn.Flex.GCaMP6f.WPRE.SV40 (Addgene). Fresh feeding medium can be added to the culture every 3-4 days.

According to the embodiments of the present disclosure, thermal imaging includes the SRR being placed in a plastic dish and immersed in PBS, for example. As an illustrative example, the MW waveguide can be oriented with H field perpendicular to the ring plane. MW can be delivered for 1 s at the resonance frequency and 2 W/cm$^2$. Imaging can be performed using a thermal camera (A325sc, FLIR). Video can be captured at a frame rate of 30 Hz for 10 s. According to the embodiments of the present disclosure, calcium imaging can be performed on, for example, a lab-built microscope based on an Olympus IX71 microscope frame with a 20× air objective (UPLSAPO20X, 0.75 NA, Olympus). The sample can be illuminated by a 470 nm LED (M470L2, Thorlabs), with an emission filter (FBH520-40, Thorlabs), an excitation filter (MF469-35, Thorlabs), and a dichroic mirror (DMLP505R, Thorlabs). According to the illustrative example, a scientific CMOS camera (Zyla 5.5, Andor) can be used to collect images at 20 frames per second.

According to the embodiments of the present disclosure, all experimental procedures and illustrative embodiments and examples comply with all relevant guidelines and ethical regulations for animal testing and research established and approved by the Institutional Animal Care and Use Facility of Boston University. Relating to the system and methods of the present disclosure, C57BL/6J mice aged 14-16 weeks can be anaesthetized using 5% isoflurane in oxygen then maintained with 1.5-2% isoflurane via nose cone throughout the procedure and experiment. Tail pinch can be used to monitor anaesthetization throughout, and body temperature can be maintained with a heat pad. The hair and skin on the dorsal surface can be removed. A craniotomy can be performed using a dental drill to remove a ~3 mm diameter patch of skull over the right hemisphere. Saline can be applied to immerse the brain. In relevant experiments, the TiSRR can be placed on the cortical surface over the injection site. After seizure induction and MW treatment, mice can be perfused with saline and 10% formalin. The brain can be removed, paraffin embedded, sectioned, and H&E stained for histology.

According to the embodiments of the present disclosure, seizure induction and electrocorticogram recording are included. As an illustrative example, seizures can be chemically induced by injecting 10 nL of 100 mM picrotoxin in DMSO into the cortex at AP-2, ML+2, DV+0.5, where bregma can be calibrated to be coordinate (0,0). PTZ can be injected using a motorized stereotaxic system (Stoelting) at a rate of 5 nL/min. The needle can be kept in place for 2 min after injection. A tungsten microelectrode (0.5 to 1 MΩ, Microprobes) can be inserted for LFP recording at the injection site. Extracellular recordings can be acquired using a Multiclamp 700B amplifier (Molecular Devices) filtered at 0.1 to 100 Hz, digitized with an Axon DigiData 1550 digitizer (Molecular Devices), and denoised with a D400 Multi-channel 60 Hz Mains Noise Eliminator.

According to the embodiments of the present disclosure, MW treatment can be generated, for example, using a microwave signal generator (9 kHz to 3 GHz, SMB100A, Rohde & Schwarz) connected to a solid-state power amplifier (ZHL-100W-242+, Mini Circuits) to amplify the MW to 100 W peak power. MW can be delivered from a 50 cm$^2$ waveguide (WR430, Pasternack) oriented with H field perpendicular to the SRR at the resonance frequency of the SRR. The waveguide can be ~2 cm from the SRR. Pulse modulation can be achieved using a function generator (33220A, Agilent). In vivo, one round of treatment can consist of 10 s of 0.5 W/cm$^2$ MW at 2.05 GHz with pulse width 10 ms and repetition rate 100 Hz.

According to the embodiments of the present disclosure, calcium images can be analyzed using, for example, ImageJ. The somata of neurons can be selected for fluorescence measurement. Calcium traces, temperature traces, and electrophysiological traces can be analyzed using, for example, Origin 2018. All statistical analysis can done using two-sample t-test, with data shown are mean±SD.

The microwave SRR of the present disclosure is a novel platform for wireless, battery-free neuromodulation in the deep brain with high spatial precision. The device operates within safety limits and occupies a volume <2 mm3. Other applications of the device might include, but are not limited to, making the implant a rod so that it may be injected into the brain, or being applied to other conditions, such as chronic pain or Parkinson's Disease. Additionally, applications of the present disclosure might include, but are not limited to, multiple SRRs with varying diameter implanted to modulate multiple brain regions in sequence, or utilizing the thermal stimulation capabilities of the SRR at power densities around 3 W/cm2 for use on its own or in conjunction with inhibition.

Whereas many alterations and modifications of the disclosure will become apparent to a person of ordinary skill in the art after having read the foregoing description, it is to be understood that the particular embodiments shown and described by way of illustration are in no way intended to be considered limiting. Further, the subject matter has been described with reference to particular embodiments, but variations within the spirit and scope of the disclosure will occur to those skilled in the art. It is noted that the foregoing examples have been provided merely for the purpose of explanation and are in no way to be construed as limiting of the present disclosure.

While the present inventive concept has been particularly shown and described with reference to exemplary embodiments thereof, it will be understood by those of ordinary skill in the art that various changes in form and details may be made therein without departing from the spirit and scope of the present inventive concept as defined by the following claims.

What is claimed is:

1. A system for neuromodulation, comprising:
   a split-ring resonator (SRR) comprising a resonance circuit, the SRR being implantable in a target site; and
   a source of microwave signals, wherein the microwave signals are deliverable wirelessly to couple with the SRR to produce a localized electrical field,
   wherein the localized electrical field modulates one or more neurons at the target site.

2. The system of claim 1, wherein the SRR is powered wirelessly by the microwave signals.

3. The system of claim 1, wherein the SRR has a perimeter of approximately one half of the microwave signal wavelength and functions as a resonant antenna.

4. The system of claim 1, wherein the SRR has a volume of no more than 1.8 mm$^3$.

5. The system of claim 1, wherein the localized electrical field enables region-specific brain modulation.

6. The system of claim 1, wherein the localized electrical field enables inhibition of a single nerve.

7. The system of claim 1, wherein the localized electrical field modulates one or more neurons with submillimeter wavelength spatial precision.

8. The system of claim 1, wherein the submillimeter wavelength spatial precision is in the order of 100 μm.

9. The system of claim 1, wherein the SRR enables lower microwave dosage to meet safety limits of 10 W/kg averaged over 6 minutes, which corresponds to an average dosage of 3600 J/kg.

10. The system of claim 9, wherein the lower microwave dosage prevents thermal damage.

11. The system of claim 1, wherein the source of microwave signals is adjusted to tune a resonance frequency of the SRR.

12. The system of claim 1, wherein the SRR comprises at least one of the following: copper; and titanium alloy.

13. The system of claim 1, wherein the microwave signals are pulsed signals, and the microwave signals can undergo pulse modification to prolong microwave treatment without inducing thermal toxicity.

14. The system of claim 1, wherein the system comprises multiple SRRs with varying diameter for implanting at multiple target sites to modulate multiple regions.

15. The system of claim 1, wherein the microwave signals are delivered at dosages below the safe exposure limit.

16. The system of claim 1, wherein the localized electrical field stimulates one or more neurons at the target site.

17. The system of claim 1, wherein the localized electrical field inhibits one or more neurons at the target site.

18. The system of claim 1, wherein the localized electrical field is configured to allow for stimulation and inhibition of one or more neurons at the target site.

19. The system of claim 1, wherein the SRR includes thermal stimulation capabilities.

20. The system of claim 19, wherein the thermal stimulation capabilities of the SRR are at power densities of around 3 W/cm2.

21. A system for neuromodulation, comprising:
a split-ring resonator (SRR) comprising a resonance circuit, the SRR being implantable in a target site; and
a source of microwave signals, wherein the microwave signals are deliverable wirelessly to couple with the SRR to produce a localized electrical field,
wherein the localized electrical field allows for modulation, including stimulation and inhibition, of one or more neurons at the target site.

22. The system of claim 21, wherein the SRR is powered wirelessly by the microwave signals.

23. The system of claim 21, wherein the SRR has a perimeter of approximately one half of the microwave signal wavelength and functions as a resonant antenna.

24. The system of claim 21, wherein the SRR has a volume of no more than 1.8 mm³.

25. The system of claim 21, wherein the localized electrical field enables region-specific brain modulation.

26. The system of claim 21, wherein the localized electrical field enables inhibition of a single nerve.

27. The system of claim 21, wherein the localized electrical field modulates one or more neurons with submillimeter wavelength spatial precision.

28. The system of claim 21, wherein the submillimeter wavelength spatial precision is in the order of 100 μm.

29. The system of claim 21, wherein the SRR enables lower microwave dosage to meet safety limits of 10 W/kg averaged over 6 minutes, which corresponds to an average dosage of 3600 J/kg.

30. The system of claim 29, wherein the lower microwave dosage prevents thermal damage.

31. The system of claim 21, wherein the source of microwave signals is adjusted to tune a resonance frequency of the SRR.

32. The system of claim 21, wherein the SRR comprises at least one of the following: copper; and titanium alloy.

33. The system of claim 21, wherein the microwave signals are pulsed signals, and the microwave signals can undergo pulse modification to prolong microwave treatment without inducing thermal toxicity.

34. The system of claim 21, wherein the system comprises multiple SRRs with varying diameter for implanting at multiple target sites to modulate multiple regions.

35. The system of claim 21, wherein the microwave signals are delivered at dosages below the safe exposure limit.

36. The system of claim 21, wherein the SRR includes thermal stimulation capabilities.

37. The system of claim 36, wherein the thermal stimulation capabilities of the SRR are at power densities of around 3 W/cm2.

38. A method for neuromodulation comprising:
implanting, in a target site, a split-ring resonator (SRR) comprising a resonance circuit; and
delivering microwave signals wirelessly to the SRR to produce a localized electrical field,
wherein the localized electrical field modulates one or more neurons at the target site.

39. The method of claim 38, further comprising, powering the SRR wirelessly via the microwave signals.

40. The method of claim 38, wherein the microwave signals are delivered at an average dosage lower than 10 W/kg averaged over 6 minutes, which corresponds to an average dosage of 3600 J/kg.

41. The method of claim 38, further comprising adjusting the microwave signals to tune a resonance frequency of the SRR.

42. The method of claim 38, further comprising pulsing the microwave signals, wherein the microwave signals undergo pulse modification to prolong microwave treatment without inducing thermal toxicity.

43. A method for neuromodulation comprising:
implanting, in a target site, a split-ring resonator (SRR) comprising a resonance circuit; and
delivering microwave signals wirelessly to the SRR to produce a localized electrical field,
wherein the localized electrical field allows for stimulation and inhibition of one or more neurons at the target site.

44. The method of claim 43, further comprising, with the localized electrical field, stimulating the one or more neurons at the target site.

45. The method of claim 43, further comprising, with the localized electrical field, inhibiting the one or more neurons at the target site.

46. The method of claim 43, further comprising, powering the SRR wirelessly via the microwave signals.

47. The method of claim 43, wherein the microwave signals are delivered at an average dosage lower than 10 W/kg averaged over 6 minutes, which corresponds to an average dosage of 3600 J/kg.

48. The method of claim 43, further comprising adjusting the microwave signals to tune a resonance frequency of the SRR.

49. The method of claim 43, further comprising pulsing the microwave signals, wherein the microwave signals undergo pulse modification to prolong microwave treatment without inducing thermal toxicity.

* * * * *